US006653527B1

(12) United States Patent
Deng et al.

(10) Patent No.: US 6,653,527 B1
(45) Date of Patent: Nov. 25, 2003

(54) PRODUCTION OF HEALTHIER AND STRONGER SEEDLING CROPS UNDER LOW-LIGHT ENVIRONMENT

(75) Inventors: Xing Wang Deng, Hamden, CT (US); Timothy McNellis, Berkeley, CA (US); Keiko Torii, Ypsilanti, MI (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/145,977

(22) Filed: Sep. 3, 1998

Related U.S. Application Data

(60) Provisional application No. 60/057,423, filed on Sep. 3, 1997.

(51) Int. Cl.[7] .......................... A01H 1/00; A01H 11/00; C12P 21/06; C07H 21/04
(52) U.S. Cl. ....................... 800/278; 800/290; 800/295; 800/298; 800/306; 800/313; 800/317; 800/317.4; 800/320; 800/320.2; 435/69.1; 435/468; 435/410; 435/419; 435/252.3; 435/320.1; 536/23.1; 536/23.2; 536/23.4; 536/23.6
(58) Field of Search ............................... 435/69.1, 468, 435/410, 419, 252.3, 320.1; 536/23.1, 23.2, 23.4, 23.6; 800/278, 290, 295, 298, 306, 313, 317, 317.4, 320, 320.2

(56) References Cited

U.S. PATENT DOCUMENTS 5,736,627 A * 4/1998 Loesch-Fries et al. ... 435/252.2

FOREIGN PATENT DOCUMENTS

WO  WO 97/35986   10/1997

OTHER PUBLICATIONS

NCBI—MeSH Brower (http://www.ncbi.nlm.nih.gov.80/entrez/meshbrowser.cgi?retrievestring=&mbdetail=n&term=mutation).*
pir60 Accession No. NO:A44272.*
Lazar et al. (Molecular and Cellular Biology, Mar. 1988, vol. 8, No. 3, p. 1247–1252).*
Burgess et al. (The Journal of Cell Biology, 1990, vol. 111, p. 2129–2138).*
Broun et al. (Science, Nov. 13, 1998, vol. 282, p. 131–133).*
Lederman et al. (Molecular Immunology (1991) 28(11):1171–1181).*
Goodenough, U. (Genetics 2nd Edition (1978) pp. 328–329.*
Ang, L. –H. and Deng, X. –W. (1994). Regulatory hierarchy of photomorphogenic loci: allele–specific and light–dependent interaction between the HY5 and COP1 loci. *Plant Cell* 6, 613–628.
Deng, "Fresh View of Light Signal Transduction in Plants," *Cell*, vol. 76, 423–426, 1994.

Deng, X.–W. and Quail, P.H. (1992). Genetic and phenotypic characterization of cop1 mutants of *Arabidopsis thaliana*. *Plant J.* 2, 83–95.
Deng, X.–W., Matsui, M., Wei, N., Wagner, D., Chu, A. M., Feldmann, K. A. and Quail, P.H. (1992). *COP1*, and Arabidopsis regulatory gene, encodes a protein with both a zinc–binding motif and a $G_{p\beta homologous\ domain}$. *Cell* 71, 791–801.
Deng, X.–W., Caspar, T., and Quail, P.H. (1991). cop1: A regulatory locus involved in light–controlled development and gene expression in Arabidopsis. *Genes Dev.* 5, 1172–1182.
Frances, S., White, M.J., Edgerton, M.D., Jones, A.M., Elliott, R.C. and Thompson, W.F. (1992). Initial characterization of a pea mutant with light–independent photomorphogenesis. *The Plant Cell* 4(12), 1519–130.
Frances, S., Matsui, M., Kendrick, R.E., and Deng, X.–W. (1997) A tomato homologue of the Arabidopsis COP1 gene exhibits a novel pattern of expression. *ESOP Programme and Abstracts*. European Symposium on Photomorhogenesis, Jul. 12–18.
McNellis et al. (1996) "Expression of an N–Terminal Fragment of COP1 Confers a Dominant–Negative Effect on Light–Regulated Seedling Development in Arabidopsis," *The Plant Cell*, vol. 8, 1491–1503.
McNellis, T. W., and Deng, X.–W. (1995). Light control of seedling morphogenetic pattern. *Plant Cell* 7, 1749–1761.
McNellis, T. W., von Arnim, A. G., and Deng, X.–W. (1994). Overexpression of Arabidopsis COP1 results in partial suppression of light mediated development: evidence for a light–inactivable repressor of photomorphogenesis. *Plant Cell* 6, 1391–1400.
McNellis, T.W., von Arnim, A. G., Araki, T., Komeda, Y., Miséra, S. and Deng, X.–W. (1994). Genetic and molecular analysis of an allelic series of cop1 mutants suggests functional roles for the multiple protein domains. *Plant Cell* 6, 487–500.
Tomohiko, T. Yoshizumi, T., Deng, X.–W., and Matsui, M. (1997). Isolation and characterization of Arabidopsis COP1 homologous gene in rice. *ESOP Programme and Abstracts*. European Symposium on Photomorhogenesis, Jul. 12–18, 1997.

(List continued on next page.)

Primary Examiner—Phuong T. Bui
Assistant Examiner—Alexander H. Spiegler
(74) Attorney, Agent, or Firm—Morgan, Lewis & Bockius LLP

(57) ABSTRACT

This invention relates to seedlings which demonstrate improved phenotypic characteristics when grown at low light levels. More specifically, the present invention relates to producing plants which contain a nucleic acid sequence coding for the N282 protein as well as the wildtype COP1 gene.

12 Claims, 11 Drawing Sheets

OTHER PUBLICATIONS von Arnim, A. G. and Deng, X.–W. (1994). Light activation of Arabidopsis photomorphogenic COP1 involves a cell-–specific regulation of it nucleo–cytoplasmic partitioning. *Cell* 79, 1035–1045.

von Arnim, A. G., and Deng, X.–W. (1993). Ring–finger motif of *Arabidopsis thaliana* COP1 defines a new class of zinc–binding domain. *J. Biol. Chem.* 268, 19626–19631.

Zhao, L., W. Chunxia, Y. Zhu, J. Zhao, and Wu, X. (1998). Molecular cloning and sequencing of the cDNA of cop1 gene from *Pisium sativum. Biochimica et Biophysica Acta* 1395, 326–328.

Ang et al., Plant Cell, 6, 613–628.

Deng et al., 1991, Genes Dev. 5, 1172–1182.

Deng et al., 1992, Plant J. 2, 83–95.

Deng et al., 1992, Cell 71, 791–801.

Deng et al., 1994, Cell, 76: 423–426.

Frances et al., 1992, The Plant Cell, 4(12):1519–530.

Frances et al., 1997, ESOP Programme and Abstracts, European Symposium on Photomorphogenesis, Jul. 12–18, Abstract No. 489.

Goodenougt, U., 1978, Genetics 2nd edition, 328–329.

Kwok et al., 1996, Plant Physiol. 110, 731–742.

Lupas et al., 1996, TIBS, 21, 375–382.

McNellis et al., 1995, Plant Cell 7, 1749–1761.

McNellis et al., 1994, Plant Cell 6, 487–500.

McNellis et al., 1996, Plant Cell, 8, 1491–1503.

Matsui et al., 1995, Proc. Natl. Acad. Sci. USA, 92, 4239–4243.

NCBI—MeSH Brower (http://www.ncbi.nlm.nih.gov:80/entrez/meshbrowser.gi?restrievestring=& mbdetail=n&term=mutation).

Neer etal., 1994, Nature 371, 297–300.

pir 60 Accession No. A44272 dated Apr. 30, 1993.

Staub et al., 1996, Plant Cell, 8, 2047–2056.

Tomohiko et al., 1997, ESOP Programme and Abstracts. European Symposium on Photomorphogenesis, Jul. 12–18, 1997.

Torii et al., 1998, The EMBO Journal, vol. 17, pp. 5577–5587.

U.S. Application No. 09/407,956, filed Sep. 28, 1999.

Von Arnim et al., 1993, J. Biol. Chem. 268, 19626–19631.

Von Arnim et al., 1994, Cell 79, 1035–1045.

Von Arnim et al., 1997, Plant Physiol. 114, 770–788.

Wei et al., 1996, Plant Physiol. 112, 871–878.

Yamamoto et al., 1998, Biochemica et Biophysica Acta 1395, 326–328.

Zhao et al., 1998, Plant Cell. 10, 1083–1094.

Zhou et al., 1998,. Mol. Gen. Genet. 257, 387–391.

* cited by examiner

A.

B.

A. White Light

B. Dark

```
  1 CAAAAACCAAAATCACAATCGAAGAAATCTTTTGAAAGCAAAATGGAAGAGATTTCGACGGATCCGGTTGTT
                                              M  E  E  I  S  T  D  P  V  V

73 CCAGCGGTGAAACCTGACCCGAGAACATCTTCAGTTGGTGAAGGTGCTAATCGTCATGAAAATGACGACGGA
 11  P  A  V  K  P  D  P  R  T  S  S  V  G  E  G  A  N  R  H  E  N  D  D  G

145 GGAAGCGGCGGTTCTGAGATTGGAGCACCGGATCTGGATAAAGACTTGCTTTGTCCGATTTGTATGCAGATT
 35  G  S  G  G  S  E  I  G  A  P  D  L  D  K  D  L  L  C  P  I  C  M  Q  I

217 ATTAAAGATGCTTTCCTCACGGCTTGTGGTCATAGTTTCTGCTATATGTGTATCATCACACATCTTAGGAAC
 59  I  K  D  A  F  L  T  A  C  G  M  S  F  C  Y  M  C  I  I  T  H  L  R  N

289 AAGAGTGATTGTCCCTGTTGTAGCCAACACCTCACCAATAATCAGCTTTACCCTAATTTCTTGCTCGATAAG
 83  K  S  D  C  P  C  C  S  Q  H  L  T  N  N  Q  L  Y  P  N  F  L  L  D  K

361 CTATTGAAGAAAACTTCAGCTCGGCATGTGTCAAAAACTGCATCGCCCTTGGATCAGTTTCGGGAAGCACTA
107  L  L  K  K  T  S  A  R  H  V  S  K  T  A  S  P  L  D  Q  F  R  E  A  L

433 CAAAGGGGTTGTGATGTGTCAATTAAGGAGGTTGATAATCTTCTGACACTTCTTGCGGAAAGGAAGAGAAAA
131  Q  R  G  C  D  V  S  I  K  E  V  D  N  L  L  T  L  L  A  E  R  K  R  K

505 ATGGAACAGGAAGAAGCTGAGAGGAACATGCAGATACTTTTGGACTTTTTGCATTGTCTAAGGAAGCAAAAA
155  M  E  Q  E  E  A  E  R  N  M  Q  I  L  L  D  F  L  H  C  L  R  K  Q  K

577 GTTGATGAACTAAATGAGGTGCAAACTGATCTCCAGTATATTAAAGAAGATATAAATGCCGTTGAGAGACAT
179  V  D  E  L  N  E  V  Q  T  D  L  Q  Y  I  K  E  D  I  N  A  V  E  R  H

649 AGAATAGATTTATACCGAGCTAGGGACAGATATTCTGTAAAGTTGCGGATGCTCGGAGATGATCCAAGCACA
203  R  I  D  L  Y  R  A  R  D  R  Y  S  V  K  L  R  M  L  G  D  D  P  S  T

721 AGAAATGCATGGCCACATGAGAAGAACCAGATTGGTTTCAACTCCAATTCTCTCAGCATAAGAGGAGGAAAT
227  R  N  A  W  P  H  E  K  N  Q  I  G  F  N  S  N  S  L  S  I  R  G  G  N

793 TTTGTAGGCAATTATCAAAACAAAAAGGTAGAGGGGAAGGCACAAGGAAGCTCTCATGGGCTACCAAAGAAG
251  F  V  G  N  Y  Q  N  K  K  V  E  G  K  A  Q  G  S  S  H  G  L  P  K  K

865 GATGCGCTGAGTGGGTCAGATTCG
275  D  A  L  S  G  S  D  S
```

PRODUCTION OF HEALTHIER AND STRONGER SEEDLING CROPS UNDER LOW-LIGHT ENVIRONMENT

CROSS REFERENCES TO RELATED APPLICATIONS

This application is a continuation-in-part application of U.S. Provisional Patent Application No. 60/057,423, filed on Sep. 3, 1997, which is herein incorporated by reference in its entirety.

STATEMENT OF RIGHTS TO INVENTIONS MADE UNDER FEDERALLY SPONSORED RESEARCH

This invention was partially made with government support under National Institutes of Health Grant No. GM47850.

FIELD OF THE INVENTION

The present invention pertains, in general, to the production of seedlings which demonstrate improved plant characteristics when grown under low light conditions. In particular, the present invention pertains to modifying the genotypes of plant cells to include a sequence coding for the N282 protein.

BACKGROUND OF THE INVENTION

All publications and patent applications herein are incorporated by reference to the same extent as if each individual publication or patent application was specifically and individually indicated to be incorporated by reference.

Through photosynthesis, light provides the energy source for plants and, ultimately, for all living organisms. The light environment plays a crucial role in plant growth and development. Besides serving as a source of energy, light provides signals to regulate many complex developmental processes. At least three photoreceptor families—pytochromes (red and far-red light), blue light receptors, and UV light receptors—mediate these light-regulated developmental processes. Light signals perceived by specific photoreceptors are transduced via signaling components to bring about the diverse downstream physiological responses, including seed germination, stem elongation, chloroplast and leaf development, floral induction, and coordinated expression of many light-regulated nuclear- and chloroplast-encoded genes.

In response to a fluctuating environment, the nonmobile plant must be able to sense varying light signals and to optimize growth and development. Higher plants possess sophisticated photosensory and signal transduction systems to monitor the direction, quantity, and quality of the light signal and to adjust their growth and development through regulated gene expression at every stage of their life cycle, such as germination, seedling development, and flowering. These light-regulated developmental processes are collectively termed photomorphogenesis.

Plant development is a highly malleable process that is strongly influenced by environmental factors, especially light. The effects of light on plant development are especially prominent at the seedling stage (Kendrick and Kronenberg, 1994; McNellis and Deng, 1995). As compared with plants grown in light, those grown in darkness are white or yellow in color, the internodes are long, the leaves are very much reduced in size, and the root systems are poorly developed. This condition is known as etiolation. Of course, etiolated seedlings cease growth when their reserve food supply is exhausted.

The light environment in nature is complex. Unobstructed sunlight consists of a wide continuum of photon wavelengths that is conveniently divided into three large spectral domains: UV (<400 nm), visible (400 to 700 nm) and far-red (>700 nm) light. The spectral quality, or relative photon distribution, at different wavelengths can vary greatly, depending on the location and the time of day. For example, within the canopy, the light available is essentially depleted in the visible and UV regions, and far-red light is highly represented. Furthermore, twilight normally has a higher far-red to red ratio than daylight. Although higher plants effectively utilize only visible light for photosynthesis, they have the capability to sense and respond to a much wider range of the spectrum, including UV and far-red light.

In a photochemical process such as photosynthesis, the end product depends upon the number of quanta absorbed rather than the total light energy absorbed. A single red photon has the same effect in photosynthesis as a, single blue photon, for example, although the blue photon has more energy. Hence, in the recent literature it has become common to refer to the number of photons per unit area per unit time. Einsteins (for photosynthesis) or microeinsteins (for low light responses) are used. While an open field during a mid-summer day may receive as much as 2,000 microeinsteins per square meter per hour, the same area in an indoor room with fluorescent lamps may only receive 50 to 100 microeinsteins in the same time period. When the open field has its light blocked by smog, clouds or rain, it may actually register less photons per unit area per unit time than the indoor room.

In general, absence of light increases, and presence of light decreases, the rate at which the stems elongate. Thus, the features associated with etiolation ensure, under natural conditions, that the shoot is carried towards the light as rapidly as possible. Such a physiological and morphological response to the complete lack of light is critical for the growth and eventual emergence of the seedling from the position where the seed is planted in the soil or other growth media.

However, under some conditions of low natural light, such as would result from a succession of cloudy or rainy days or from an inability to supply high levels of artificial light in the greenhouse, etiolation can cause plant husbandry problems. For example, etiolated seedlings tend to fall over easily and to produce weaker plants which are more susceptible to pests, such as aphids and spider mites, and to other environmental challenges, such as wind or waterlogged pots or fields. Under such conditions, the etiolated seedlings may develop into less vigorous adult plants, produce less reproductive structures and fewer offspring, or even perish. If a sufficient number of seedlings or plants are adversely affected by the etiolation effect, this may result in reduced production of a particular plant product on a per surface area yield basis. For example, the yield of tomato fruits on a per hectare or per acre basis may be dramatically reduced if severe seedling etiolation results in the formation of spindly tomato plants which lodge. Such lodging can reduce fruit size through decreased photosynthetic activity of the collapsed shoot, greatly increase fruit rotting through contact of the fruit with the soil, and lead to greater pest access and pest damage of the fruits.

Plant responses to light are especially evident in the young seedling, although they occur throughout the life of the plant. Early seedling development in Arabidopsis (*Arabidopsis thaliana*) provides an excellent model system to dissect the light signal transduction pathway in plants. As a typical dicotyledonous plant, Arabidopsis seedlings follow two distinct strategies of development, skotomorphogenesis in darkness or photomorphogenesis in light. Dark-grown seedlings have long hypocotyls, unopened apical hooks, and undeveloped (small and unopened) cotyledons. Their light-inducible genes are expressed at very low levels, and their plastids develop into etioplasts that possess no chlorophyll and are not photosynthetically competent. In contrast, light-grown seedlings have short hypocotyls, no apical hooks, open and enlarged cotyledons with developed, photosynthetically active chloroplasts and leaves, and a distinctly different pattern of gene expression from that observed in dark-grown plants. At least three families of photoreceptors, phytochromes (red and far red light), blue light receptors, and ultraviolet (UV) light receptors, are utilized to sense the different light wavelengths, and the signals transduced by these receptors coordinately regulate the transcription of specific genes.

Photomorphogenic development depends on the plant being able to detect light signals. If this ability is impaired, such as when photoreceptors are disrupted by mutations, then a growing seedling assumes a somewhat etiolated developmental pattern. For example, mutations in phytochrome A gene (PHYA) cause reduced responsiveness to far-red light signals (Dehesh et al., 1993; Nagatani et al., 1993; Parks and Quail, 1993; Whitelam et al., 1993); mutations in phytochrome B gene (PHYB) cause reduced responsiveness to red light stimulation (Reed et al., 1993; Wester et al., 1994); mutations in a putative blue light receptor gene, HY4, cause reduced responsiveness to blue light (Ahmad and Cashmore, 1993). Symptoms of reduced light responsiveness in phyA, phyB, and hy4 mutants include long hypocotyls and reduced cotyledon expansion under certain light conditions (Koornneef et al., 1980; McNellis et al., 1994b). On the other hand, photoreceptor overexpression causes hypersensitivity to the spectral quality of light that the photoreceptor primarily absorbs. For example, overexpression of PHYB causes hypersensitivity to red light (Wagner et al., 1991; McCormac et al, 1993); overexpression of PHYA causes hypersensitivity to far-red light and red light (Boylan and Quail, 1991; McCormac et al., 1991, 1992, 1993; Whilelam et al., 1992); overexpression of the CRYPTOCHROME1 (CRY1) blue light photoreceptor encoded by the HY4 locus causes hypersensitivity to blue, UV-A, and green light (Lin et al., 1995). Because of the importance of light to plant survival, it makes sense that plants have developed multiple photoreceptors with partially overlapping functions. The photoreceptors work together to monitor light signals, and stimulation of any one photoreceptor class alone appears to be sufficient to induce many aspects of seedling photomorphogenesis (Kendrick and Kronenberg, 1994; McNellis and Deng, 1995).

Several excellent reviews deal more extensively with the photoreceptor phytochromes (Quail, 1991; Furuya, 1993; Viestra, 1993), with light regulation of gene expression (Gilmartin et al., 1990; Thompson and White, 1991; Kaufman, 1993) and with photomorphogenic mutations (Chory, 1993).

The pleiotropic CONSTITUTIVE PHOTOMORPHOGENIC/DEETIOLA TED/FUSCA (COP/DET/FUS) loci may define a group of important developmental regulators specifically involved in light control of seedling morphogenesis. Mutations at all of these loci cause seedlings to exhibit essentially all aspects of photomorphogenic development in darkness (Castle and Meinke, 1994; Misera et al., 1994; Pepper et al., 1994; Wei et al., 1994; Kwok et al., 1996). Because all of the mutations at the pleiotropic COP/DET/FUS loci are recessive and cause constitutive photomorphogenic development regardless of the actual light conditions, the proteins encoded by these loci have been postulated to act as repressors of photomorphogenesis in the dark. Light signals absorbed by the various photoreceptors are thought to reverse the repressive activities of the COP/DET/FUS proteins and allow photomorphogenic development to proceed (for a recent review, see McNellis and Deng, 1995).

However, putative null mutations at all the COP/DET/FUS loci cause adult lethality and severe physiological abnormalities during seed maturation and seedling development.

This has raised concern regarding the specificity of these genes in regulating light-mediated development (Misera et al., 1994; Castle and Meinke, 1994). It is formally possible that the pleiotropic COP/DET/FUS proteins may be ubiquitous global cellular regulators and function mainly to set up the cellular environment necessary for light regulatory cascade. Although this alternative model is also consistent with the mutant phenotypes of those genes, it suggests that their gene products are not an integral part of the light regulatory cascade.

Molecular cloning of four pleiotropic COP/DET/FUS genes (Deng et al., 1992; Castle and Meinke, 1994; Pepper et al., 1994; Wei et al., 1994) has provided tools for testing those competing models.

Recently, moderate overexpression of COP1 in Arabidopsis has been shown to partially suppress blue and far-red light-mediated inhibition of hypocotyl elongation and blue light-mediated cotyledon expansion (McNellis et al., 1994b). Because those effects are the only phenotype that can be detected in those transgenic plants, it was, therefore, interpreted as evidence supporting COP1's direct involvement in the light signaling cascade. However, overexpression of full-length COP1 failed to have any detectable effect on the phytochrome B-mediated red light inhibition of hypocotyl elongation (McNellis et al., 1994b), possibly due to the low levels of overexpression. In addition, if COP1 functions directly within the light regulatory cascade and acts as a light-inactivable repressor of photomorphogenic development, ideally COP1 overexpression should also affect light control of plastid development and light-regulated gene expression. Limited overexpression of the COP1 protein (four fold or less) is clearly unable to cause detectable effect on the light-regulated gene expression and plastid development (McNellis et al., 1994b). Therefore the previous overexpression studies could not critically rule out the possibility that COP1 overexpression coincidentally influenced cell elongation in the hypocotyl and cell expansion in the cotyledon under our experimental conditions through a mechanism unrelated to photomorphogenesis.

To overcome the limitations of the full-length COP1 overexpression studies, we initiated an effort to overexpress specific mutated forms of COP1 to look for possible dominant-negative effects. COP1 is a 76.2 kD protein with an N-terminal RING-finger zinc-binding domain, followed by a putative α-helical domain, and multiple WD-40 repeats in the C-terminal half that are similar to the β subunit of trimeric G-proteins (Deng et al., 1992; McNellis et al., 1994a). The complete nucleotide and amino acid sequence of COP1 was previously provided by Deng et al. (1992b) and is available as NCBI Accession Number L24437.

To understand the structural implications of these structural motifs, 17 recessive mutations of the COP1 gene were isolated based on their constitutive photomorphogenic seedling development in darkness (McNellis et al., 1994a). One mutant type, designated as the cop1-4 mutant allele, produced a COP1 protein with only the N-terminal 282 amino acids, including both the zinc binding and the coiled-coil domains. The weak COP1-4 allele represents a C-to-T mutation that changes the Gln-283 CAA codon to a UAA stop codon. No wildtype size COP1 protein has been observed in the protein gel blot analysis of COP1-4 mutants, suggesting that translation through the newly created stop codon, if any, is negligible (McNellis et al., 1994a). The COP1-4 mutants are still capable of reacting to light to a certain degree. Dark-grown seedlings of COP1-4 develop short hypocotyls and expanded cotyledons (Ang and Deng, 1994). However, although the allele only produces a weak phenotypic defect in the seedling stage, it causes severe size reduction of light-grown plants and greatly reduced seed set (Deng and Quail, 1992).

We reasoned that the distinct structural motifs of COP1 may represent modular domains that specifically interact with upstream and downstream partners in the light regulatory cascade, if COP1 is indeed an integral part of such a signaling cascade. Overexpression of mutated COP1 proteins containing different domains would potentially compete with endogenous COP1 for interacting partners and cause dominant-negative interference with the normal COP1 function. Here, we report COP1 overexpression studies using stably transformed Arabidopsis plants containing transgenes encoding the N-terminal half of COP1, which contains both the Zn-binding motif and the putative coiled-coil domain, but depleted of the C-terminal half of COP1, which contains the entire WE-40 repeat domain. Overexpression of the N-terminal 282 amino acid fragment (N282) of COP1 caused a dominant negative interference with the ability of the endogenous wildtype COP1 to suppress multiple photomorphogenic development processes, including cellular differentiation, plastid development, and gene expression. This effect of N282 overexpression seems to be specific for light-regulated development, because it has no effect on stress—and pathogen-inducible gene expression.

Work conducted using the cop1 gene of Arabidopsis has a direct bearing on the seedling growth of other plants, including plants of agronomic and horticultural importance. For example, Frances et al. (1992) have noted that a pea (Pisum sativum) mutant with light-independent photomorphogenesis, designated lip 1, had several features in common with the deetiolated Arabidopsis mutants det1, det2 and cop1. However, the researchers also noted several important differences, including varying effects on phytochrome levels, organ-specific gene expression, plastid development and response to dark adaptation. Zhao et al. (1998) cloned and sequenced the cop1 gene from pea (NCBI Accession Number Y09579). Sequence comparison between Cop1 proteins of pea and Arabidopsis revealed that the two Cop1 proteins were highly homologous in the regions with functional domains and at the C-terminus. The two Cop1 proteins are 77.5% identical and 86.9% similar in amino acid sequences. Since pea plants display typical photomorphogenesis of the higher plants, this result demonstrates that the findings in Arabidopsis has a direct bearing on the higher plants of economic importance.

McNellis et al. (1994a) noted that the C-terminal COP1 sequence had a high degree of conservation with corresponding regions of COP1 homologs in spinach (*Spinacia olereacea*) and rice (*Oryza sativa*). The observation regarding rice was particularly interesting since the morphogenic development of monocotyledonous plants is different from that of dicotyledonous plants. Unlike dicotyledonous plants such as Arabidopsis and spinach, monocotyledonous plants such as rice exhibit extensive leaf development in darkness. Tsuge et al. (1997) showed that a COP1 homologue exists as a single copy gene in the rice genome and that the three structural domains are highly conserved between Arabidopsis and rice.

A homologue of the Arabidopsis COP1 gene has also been cloned from tomato (TCOP1) (Frances et al., 1997). The deduced amino acid sequence of the tomato gene shows high identity to the Arabidopsis gene particularly in the three defined structural motifs.

As discussed above, there exists a need for seedlings which demonstrate improved growth characteristics under low light conditions. While seedlings of the cop1-4 mutant of Arabidopsis display somewhat shorter hypocotyls when grown under low light conditions as compared to wildtype seedlings grown under the same conditions, these mutant seedlings become unhealthy, non-productive adult plants. These mutants fail to produce any COP1 protein. This invention provides seedlings which have improved phenotypic characteristics when grown under low light levels and which also grow into healthy, normal wildtype adult plants.

SUMMARY OF THE INVENTION

This invention comprises methods of altering the growth of seedlings under low light conditions. More specifically, this invention is directed to altering the growth of seedlings under low light conditions by introducing a nucleotide sequence coding for the N-terminal 282 amino acids of the COP1 gene. Alternatively, this invention is directed to altering the growth of seedlings under low light conditions by introducing a nucleotide sequence coding for both the Zn-binding motif and the putative coiled-coil domain of the COP1 gene.

As used herein, COP1 proteins and COP1 genes include the specifically identified and characterized variants herein described as well as allelic variants, conservative substitution variants and homologues that can be isolated/generated and characterized without undue experimentation following the methods outlined below. For the sake of convenience, all COP1 proteins will be collectively referred to as the COP1 proteins or the COP1 proteins of the present invention. Similarly, all COP1 genes will be collectively referred to as the COP1 genes or the COP1 genes of the present invention.

The term "COP1 proteins" or "COP1 genes" includes all naturally occurring allelic variants of the Arabidopsis COP1 protein that possess normal COP1 activity. In general, allelic variants of the COP1 protein will have a slightly different amino acid sequence than that specifically encoded by Arabidopsis COP1 gene.

As used herein, the N282 protein refers to a protein that has the amino acid sequence encoded by the polynucleotide of FIG. 11 (SEQ ID NO.2), allelic variants thereof and conservative substitutions thereof that have, N282 activity. The N282 protein is comprised of 2 subunits: the Zn-binding motif (the first underlined portion of FIG. 11) and the putative coiled-coil domain (the second underlined portion of FIG. 11), referred to herein collectively as the N282 subunits. For the sake of convenience, the collective subunits will be referred to as the N282 protein of the present invention.

The isolated nucleic acid sequences of the invention include the nucleic acid sequence encoded by SEQ ID NO: 1 (cDNA sequence of FIG. 11). in addition, the polypeptides of the invention include the protein encoded by SEQ ID NO:2 (the amino acid sequence of FIG. 11), as well as polypeptides and fragments, particularly those which have the biological activity of N282 and also those which have at least 70% sequence identity to the polypeptides encoded by SEQ ID NO:2 or the relevant portion, preferably at least 80% identity to the polypeptides encoded by SEQ ID. NO:2, and more preferably at least 90% similarity (more preferably at least 90% identity) to the polypeptides encoded by SEQ ID NO:2 and still more preferably at least 95%/o similarity (still more preferably at least 95% identity) to the polypeptides encoded by SEQ ID NO:2 and also include portions of such polypeptides.

The N282 proteins of the present invention include the specifically identified and characterized variant herein described as well as allelic variants, conservative substitution variants and homologues that can be isolated/generated and characterized without undue experimentation following the methods outlined below. For the sake of convenience, all N282 proteins will be collectively referred to as the N282 proteins or the N282 proteins of the present invention.

The term "N282 proteins" includes all naturally occurring allelic variants of the Arabidopsis N282 protein that possess normal N282 activity. In general, allelic variants of the N282 protein will have a slightly different amino acid sequence than that specifically encoded by SEQ ID NO:2 but will be able to produce the exemplified seedling phenotype under low light conditions. Allelic variants, though possessing a slightly different amino acid sequence than those recited above, will posses the ability to produce a seedling phenotype which exhibits shorter, more vigorous stems and greener, more developed leaves when compared to wildtype seedlings lacking a specific sequence coding for the N282 protein when grown under low light conditions . Typically, allelic variants of the N282 protein will contain conservative amino acid substitutions from the N282 sequences herein described or will contain a substitution of an amino acid from a corresponding position in an. N282 homologue (an N282 protein isolated from an organism other than Arabidopsis, such as rice, tomato, pea or spinach).

This invention provides plant cells which comprise a COP1 gene and, separately, a nucleotide sequence coding for the N-terminal 282 amino acids of the COP1 gene. Thus, the plant cells provided by this invention produce both the N282 protein and the wildtype COP1 protein. Wildtype, when referring to nucleic acid sequences or protein sequences, means the genetic constitution of an organism in which a number of mutations (markers) may already exist at the start of a program of mutagenesis before further changes are introduced. Thus, the wildtype COP1 protein refers to the various forms of COP1 protein found naturally before the introduction of a nucleotide sequence coding for the N-terminal 282 amino acids of the wildtype COP1 gene. This invention also provides plants produced from the plant cells of this invention.

This invention provides a plant comprising a nucleotide sequence coding for the N-terminal 282 amino acids of the COP1 gene, wherein the seedling phenotype displayed by the plant under low light conditions is characterized by shorter hypocotyls when compared to wildtype seedlings grown under the same low light conditions. The adult plant produced by the methods of this invention have approximately the same shoot size and seed set as the wildtype adult plant grown under the same conditions. Wildtype seedlings or wildtype adult plants means the standard or nonmutant form of an organism, originally indicative of the so-called natural form.

This invention also provides isolated DNA sequences encoding the N-terminal 282 amino acids of COP1.

This invention further provides vectors comprising isolated DNA sequences encoding the N-terminal 282 amino acids of COP1. This invention further provides such vectors which also include a promoter operably linked to the isolated DNA sequence.

This invention also provides host cells transformed with such vectors, wherein the host cells are prokaryotic cells, fungal cells or photosynthetic eukaryotic cells. Thus, this invention provides transgenic procaryotic, fungal or photosynthetic eukaryotic organism wherein the DNA sequence coding for the N282 protein is incorporated into the genomic DNA of the organism thereby producing transgenic organisms which produce N282 protein. More specifically, the transformed photosynthetic eukaryotic host cells provided by this invention include both monocotyledonous and dicotyledonous plants. Even more specifically, the transformed monocotyledonous and dicotyledonous plants provided by this invention include Arabidopsis, spinach, tomato, pea and rice.

This invention includes plants regenerated from the transformed plant cells as well as the progeny of such transformed plants, wherein the progeny also produce N282 protein.

This invention also provides methods of modifying the normal function of the endogenous wildtype COP1 gene by: 1) preparing vectors comprising an isolated DNA sequence encoding the N-terminal 282 amino acids of COP1 and 2) inserting the vectors into cells selected from the group consisting of prokaryotic cells, fungal cells and photosynthetic eukaryotic cells to produce transformed cells. This method further provides regenerated transformed plants produced from the transformed photosynthetic eukaryotic cells. In addition, this invention provides transformed progeny produced from the transformed regenerated plants. This invention also provides methods sexually crossing the regenerated transformed plants with other plants; harvesting the resultant seed; growing seedlings from the resultant seed under low light levels; and selecting transformed seedlings.

This invention also provides methods of producing transformed seedlings which have modified phenotypes when grown under low light conditions by: 1) preparing vectors comprising an isolated DNA sequence encoding the N-terminal 282 amino acids of COP1; 2) inserting the vectors into plant cells; 3) producing viable transformed parental plants from the transformed plant cells; and 4) growing transformed seedlings from the seed produced on the viable transformed parental plants. This invention further provides modified seedlings which display a phenotype under low light conditions which is characterized by having substantially shorter hypocotyls when compared to non-transformed, wildtype seedlings grown under the same low light conditions. Even more specifically, this invention further provides modified seedlings which display a phenotype under low light conditions which is characterized by having shorter, more vigorous stems and greener, more developed leaves when compared to non-transformed, wildtype seedlings grown under the same low light condition.

This invention also provides methods of growing crops wherein the crop includes one or more plants which contain a DNA sequence coding for the N282 protein and which also contain the indigenous wildtype COP1 gene. As used herein, the term "crop plant" means any plant grown for any commercial purpose, including, but not limited to the following purposes: seed production, hay production, ornamental use, fruit production, berry production, vegetable production, oil production, protein production, forage production, animal grazing, golf courses, lawns, flower production, landscaping, erosion control, green manure, improving soil tilth/health, producing pharmaceutical products/drugs, producing food additives, smoking products, pulp production and wood production.

One skilled in the art can easily make any necessary adjustments in accordance with the necessities of the particular situation.

Further objects and advantages of the present invention will be clear from the description that follows.

In panels A to E, the wildtype seedling is on the left, and the transgenic seedling is on the right. Different magnifications were used for each panels and the scale bar=1 mm.

Figure 3:
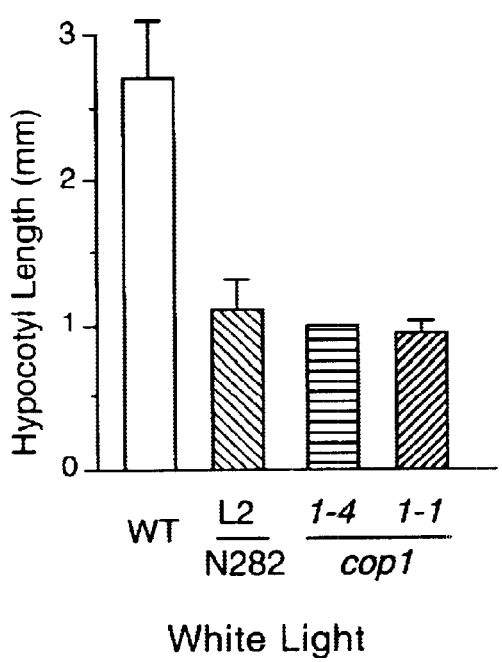
Figure 3:
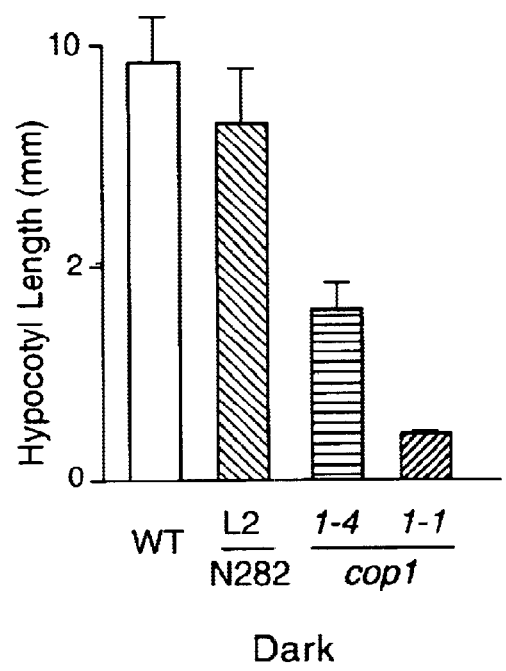

FIG. 3. The Effect of the N282 Protein on Hypocotyl Elongation in White Light and in Darkness.
  (A). The average hypocotyl lengths of wildtype (WT), N282 (L2), cop1-1, and COP1-4 seedlings after 5 days of growth in a 16 hr white light/8 hr dark photoperiod.
  (B). The average hypocotyl lengths of wildtype (WT), N282 (L2), cop1-1, and cop1-4 seedlings after 5 days of growth in darkness. The error bars indicate standard deviations from the mean. A minimum of 30 seedlings were measured for each line in each growth condition.

Figure 4:
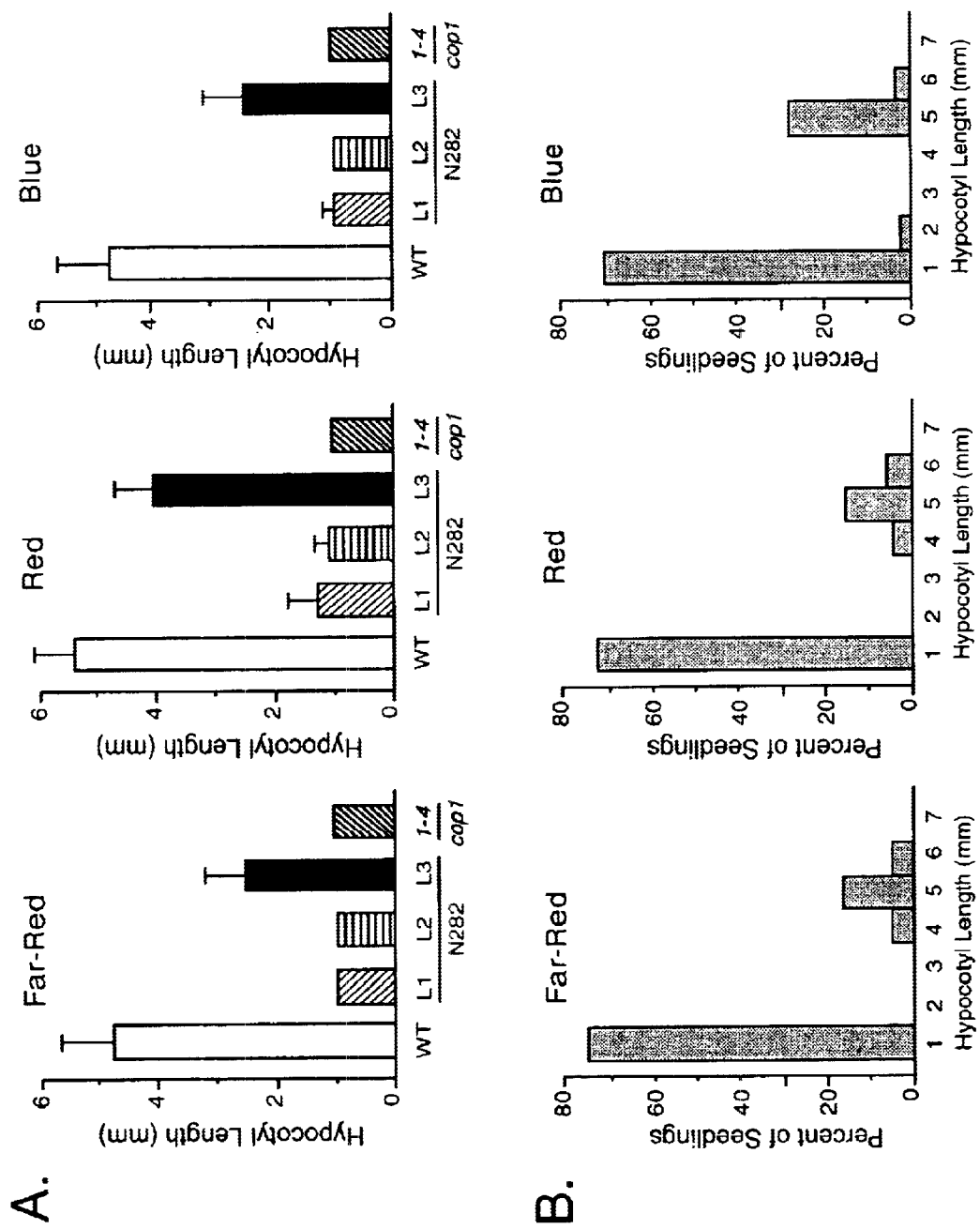

FIG. 4. The Effects of the N282 Protein on Hypocotyl Elongation in Far-Red, Red, and Blue Light.
  (A) N282 expression resulted in hypersensitivity of hypocotyl elongation to inhibition by multiple light wavelength regions. The average hypocotyl lengths of wildtype (WT) seedlings, seedlings from three representative homozygous N282 lines, and COP1-4 mutant seedlings after five days of growth in continuous far-red, red, or blue light are shown. The error bars indicate standard deviations from the mean. A minimum of 30 seedlings were measured from each line for each experiment. For details on light experiments, see McNellis et al. (1994b).
  (B) Phenotypic segregation of an N282 line (L1) heterozygous for the transgene at a single genomic locus suggested that the transgene acts in a genetically dominant manner. The seedlings were grown under continuous far-red, red, or blue light for 5 days, and the distributions of seedlings according to hypocotyl length were plotted. In each case, a short and a long hypocotyl phenotypic group was evident, and the approximately ratio of short to long was 3 to 1, as predicted for a dominant trait.

Figure 5:
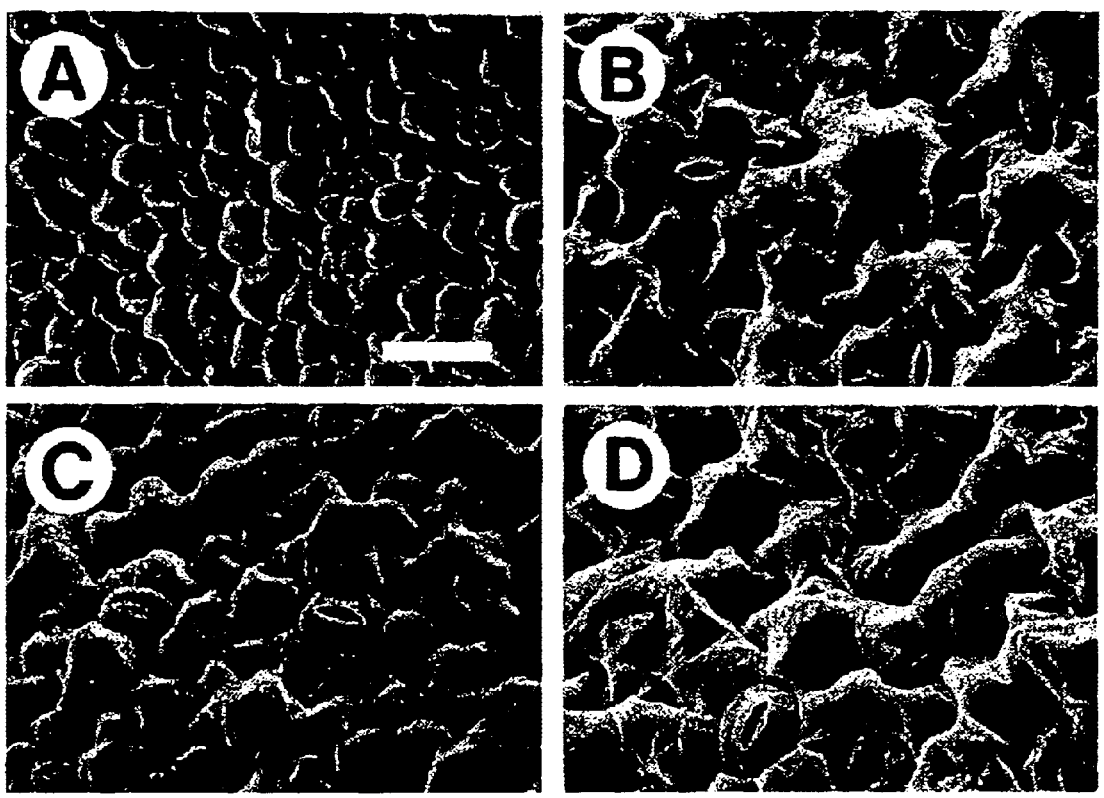

FIG. 5. Comparison of Cotyledon Epidermal Cell Differentiation Between Wildtype (WT) and N282 Transgenic Seedlings as Examined by Scanning Electron Microscopy.
  (A) A 6-day-old dark-grown wildtype seedling cotyledon.
  (B) A 6-day-old light-grown wildtype seedling cotyledon.
  (C) A 6-day-old dark-grown N282 transgenic (L2) seedling cotyledon.
  (D) A 6-day-old dark-grown cop1-4 seedling cotyledon.

The same magnification was used in (A) to (D). The scale bar in (A)=0.02 mm. In the cotyledons of dark-grown wildtype seedlings, only guard cell progenitors or immature guard cells are visible; the dark-grown N282 seedling cotyledons exhibited mature and open stomatal structures similar to those of light-grown wildtype and dark-grown cop1-4 seedlings.

Figure 6:
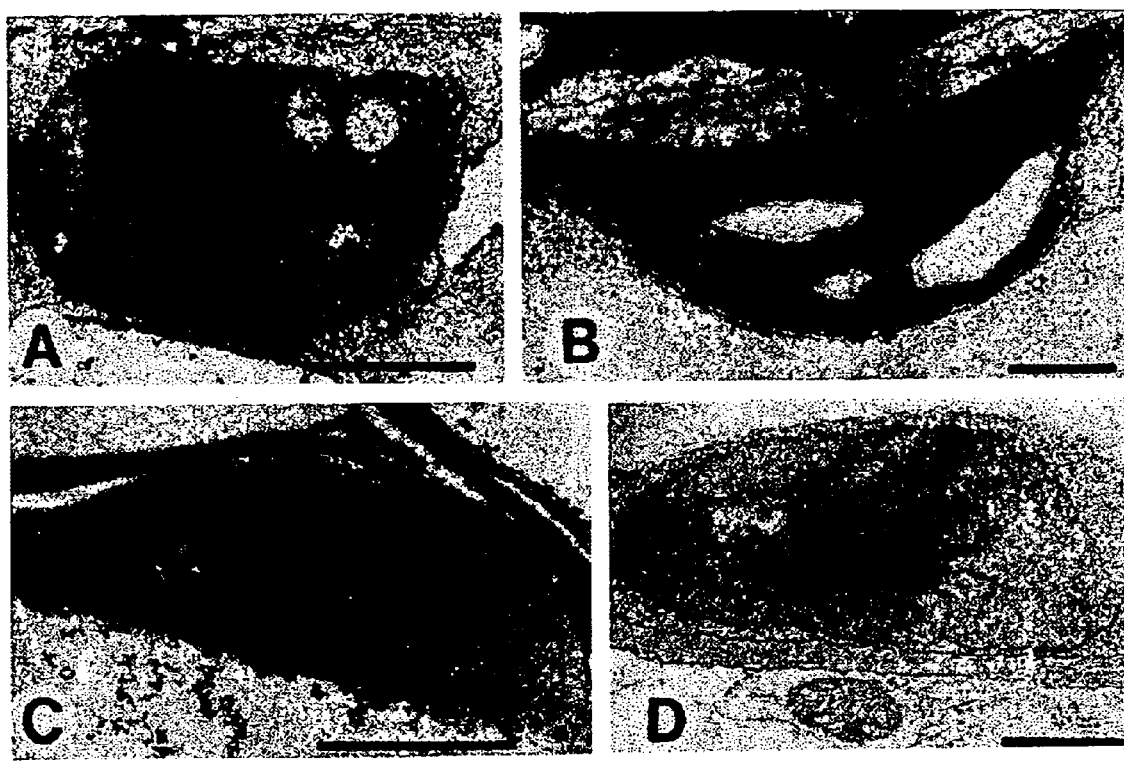

FIG. 6. Comparison of Cotyledon Plastid Differentiation Between Wildtype and N282 Transgenic Seedlings as Examined by Transmission Electron Microscopy.
  (A) A plastid from a 6-day-old dark-grown wildtype seedling.
  (B) A plastid from a 6-day-old light-grown wildtype seedling.
  (C) A plastid from a 6-day-old dark-grown N282 transgenic seedling (L2).
  (D) A plastid from a 6-day-old dark-grown COP1-4 seedling. The scale bars in each panels represents 1 µm. The plastid from dark-grown N282 seedlings lacks the prolamellar bodies of the wildtype counterpart, and it is similar to the plastid from the dark-grown cop1-4 mutant.

Figure 7:
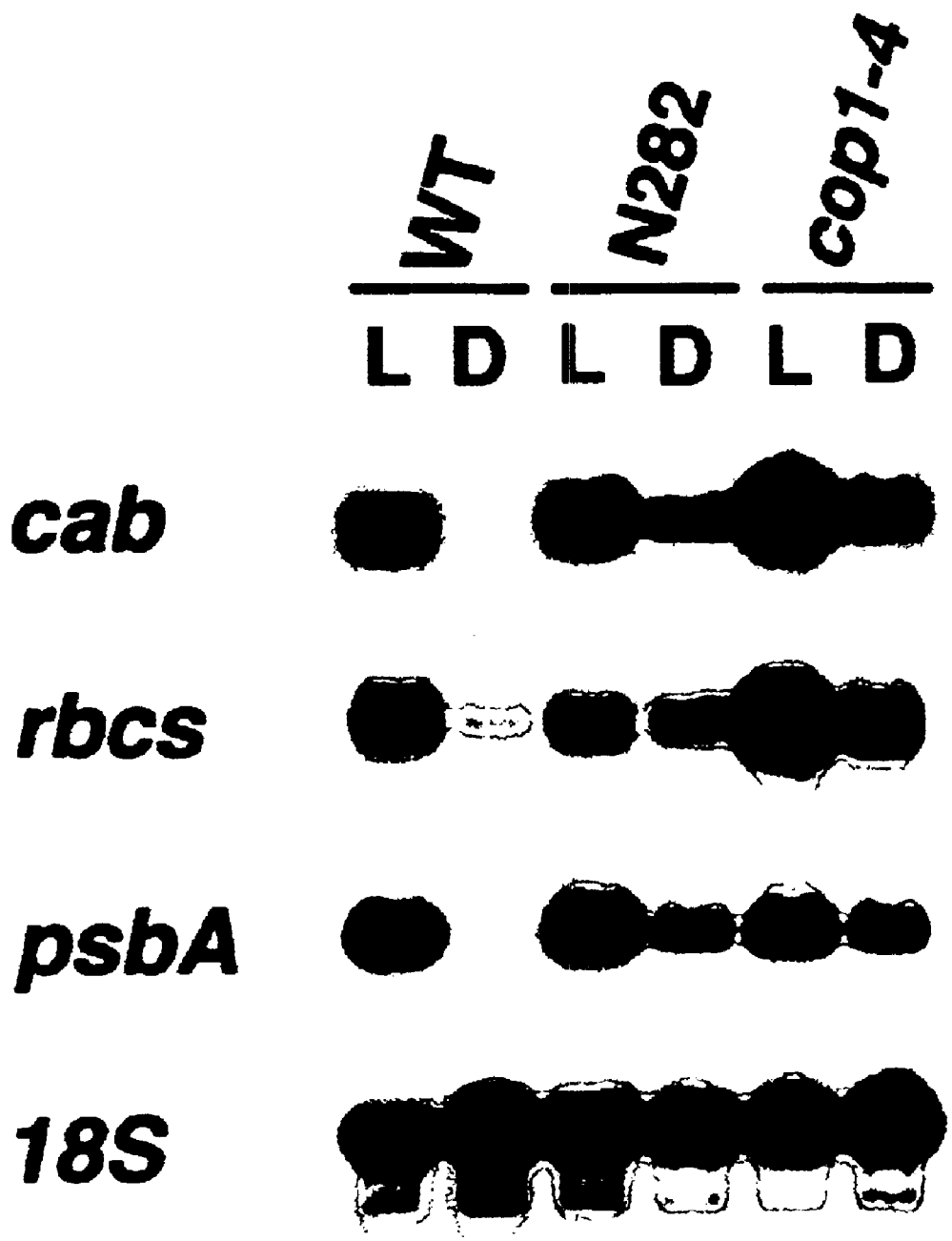

FIG. 7. The Effects of the N282 Protein on Expression of Light-Regulated Genes. RNA levels of selected genes in. 6-day-old light—(L) and dark—(D) grown seedlings were examined by RNA gel blot analysis. Equal amounts of total RNA (2.5 µg) were used in each lane. The membrane used for psbA was reprobed with the 18S rRNA probe to confirm the equal loading. For details, see Methods. WT, wildtype.

Figure 8:
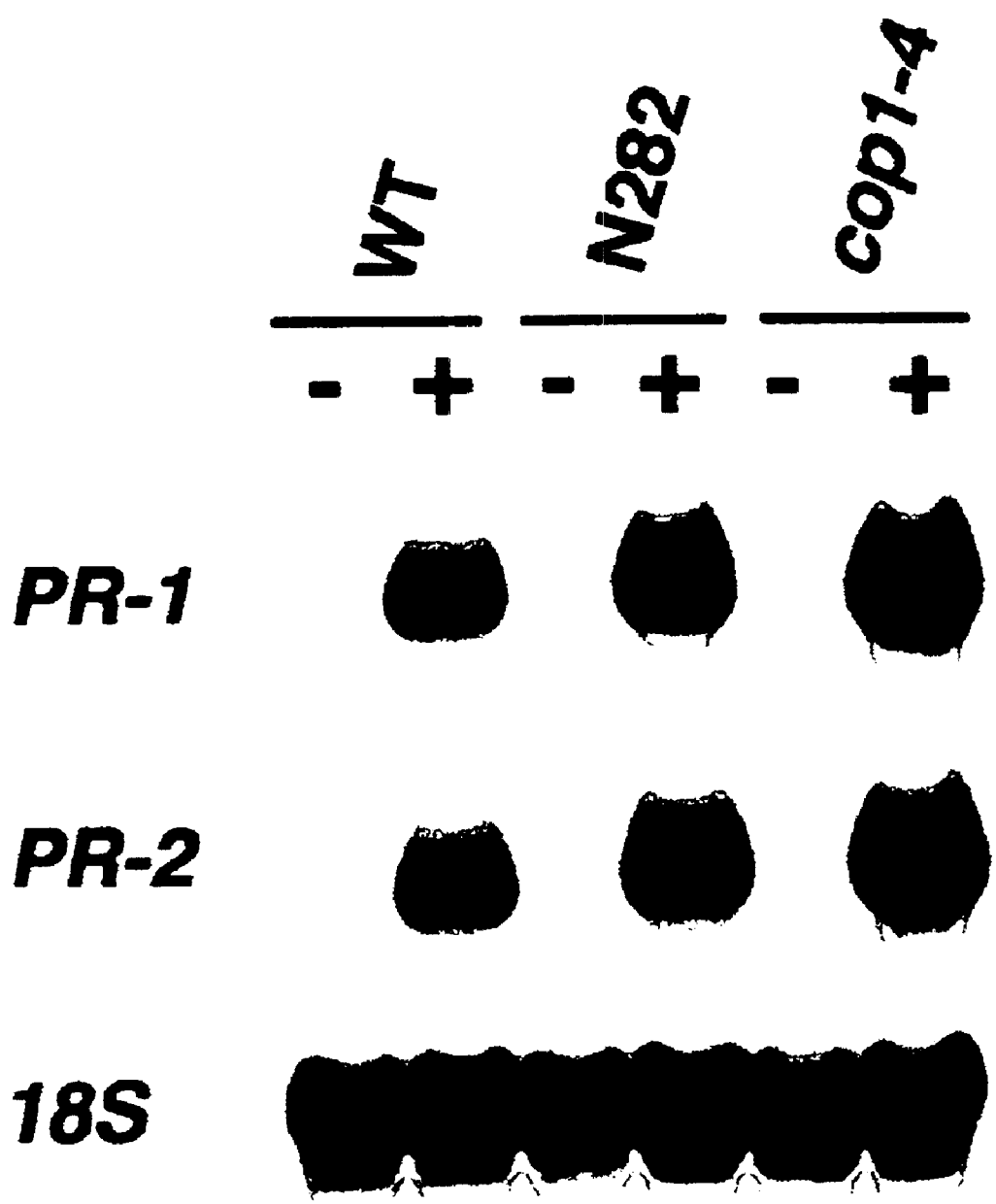

FIG. 8. The Effects of the N282 Protein and cop1-4 Mutation on Expression of Pathogen-Inducible Genes. RNA levels of selected genes in 10-day-old light-grown seedlings grown in GM medium with (+) or without (−) 0.1 mM INA were examined by RNA gel blot analysis. Equal amounts of total RNA (20 µg) were used in each lane for the PR genes. To control for equal loading, one membrane was reprobed with 18S rRNA probe. For details, see Methods. WT, wildtype.

Figure 9:
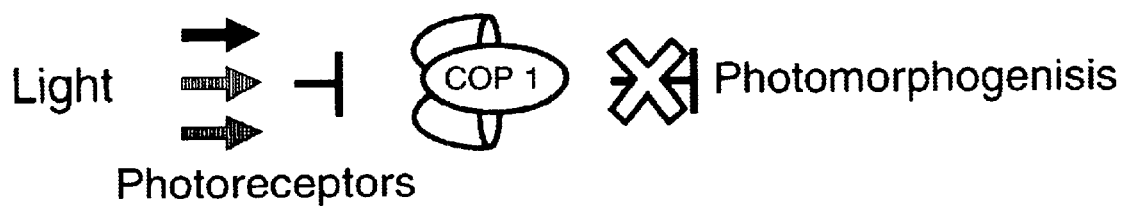
Figure 9:
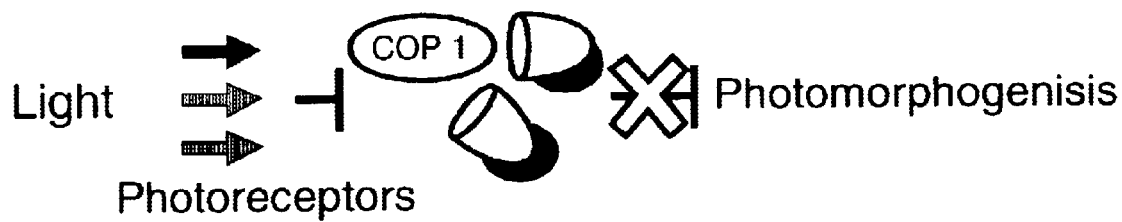

FIG. 9. Two Possible Mechanisms by Which the N282 Protein May Cause the Observed Dominant-Negative Phenotype in Transgenic Arabidopsis.
  (A) N282 may interact with endogenous wildtype COP1 and form a non-productive association and, thus, interfere with normal COP1 function.

(B) N282 may compete with wildtype COP1 for interaction with the normal COP1 downstream target(s) and, thus, inhibit normal COP1 function.

Figure 10:
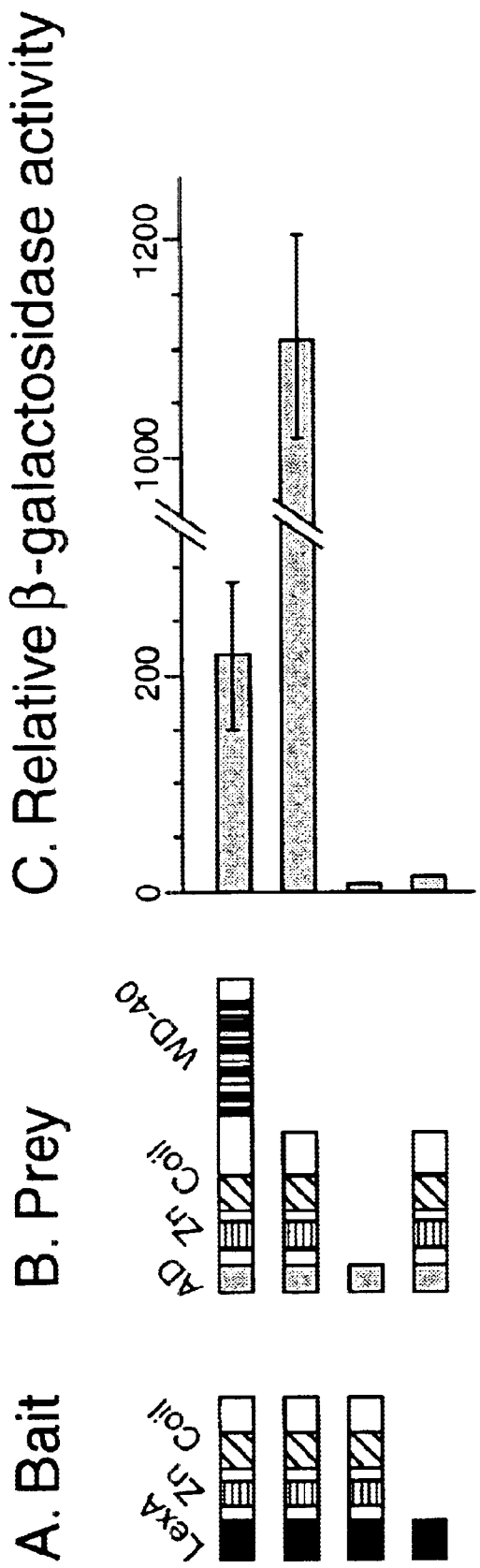

FIG. 10. N282 is Capable of Interacting with Both Full-Length COP1 and N282 Itself in the Yeast Two-Hybrid Assay.

(A) The bait constructs. The LexA DNA-binding domain was used either alone or as a fusion with N282.

(B) The prey constructs. The synthetic yeast transcription activation domain (AD) was used alone and as a fusion with N282 or full-length COP1.

(C) The relative lacZ reporter activity in yeast cells with four different combinations of bait and prey constructs as shown in (A) and (B). LacZ activity in combinations 3 and 4 represented the background levels in yeast cells. For each pairwise combination, 10 individual transformants were used to measure relative LacZ activity. Error bars represent standard deviation.

FIG. 11. The Nucleotide Sequence (SEQ ID NO:1) and Amino Acid Sequence (SEQ ID NO:2) of N282 Isolated from the cop1-4 Mutant. The two underlined sequences represent the Zn-binding motif and coiled-coil homology domains, respectively.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Overview of the Invention

As set forth above, the present invention is particularly directed to the production of plant cells, seedlings and adult plants which contain nucleic acid sequences coding for the N-terminal 282 amino acids of the COP1 gene.

This invention demonstrates that expression of N282 caused a dominant-negative phenotype in both light—and dark-grown seedlings. The expression of N282 interfered with the ability of the endogenous COP1 protein to repress photomorphogenesis and resulted in increased seedling sensitivity to a variety of light signals and partial de-etiolation in total darkness. The fact that the level of wildtype COP1 protein accumulation in the N282 transgenic seedlings did not appear to be reduced as a proportion of total protein (see FIG. 1B) clearly ruled out the possibility that cosuppression of the endogenous wildtype COP1 gene may be responsible for the observed phenotype. These phenotypic characteristics not only confirmed a specific involvement of COP1 in the light regulatory cascade, but also allowed novel insights to be made about the functional roles of the structural domains residing in the N-terminal portion of the COP1 molecule.

The Dominant-Negative Effects of N282 Suggest a Specific Role for COP1 in the Signaling Cascade Mediating Light Control of Seedling Development If COP1 is an integral part of the light signaling cascade mediating the light control of seedling development, it would be expected that a dominant-negative interference with COP1 function would lead to pleiotropic phenotypic defects that are specific for light-regulated processes. Our experimental data are entirely consistent with this prediction. In the dark, the N282 lines displayed a partial but pleiotropic photomorphogenic developmental pattern, including cotyledon cell differentiation, plastid development, and gene expression. This implies that in the transgenic plants, the endogenous wildtype, COP1 protein is unable to repress photomorphogenesis completely due to the presence of the N282 protein. Also, the N282 transgenic seedlings showed hypersensitivity of hypocotyl length inhibition under all light conditions tested, similar to that of the cop1 loss-of-function mutations. As a negative regulator of photomorphogenesis, it is hypothesized that COP1 may be inactivated to varying degrees by light signals, depending on their intensity or quantity (McNellis et al., 1994b; McNellis and Deng, 1995). The hypersensitivity of the N282 transgenic lines to light suggests that the endogenous wildtype COP1 is less efficient at inhibiting photomorphogenic responses in these lines and more easily inactivated by light. Further, the hypersensitivity of the N282 lines to far-red, red, and blue light indicates that the N282 protein renders the seedlings more sensitive to signals from multiple photoreceptors, including PHYA, PHYB, and a blue light photoreceptor. This observation is in agreement with genetic evidence from cop1 mutants and evidence from transgenic plants overexpressing full-length COP1. This result suggests that signals from multiple photoreceptors converge to modulate COP1 activity (Deng et al., 1991; McNellis et al., 1994b; McNellis and Deng, 1995). It is especially worth mentioning the effects of N282 expression on responses to red light, because the overexpression of full-length COP1 failed to cause any observable effect on red light-mediated hypocotyl elongation (McNellis et al., 1994b). The experiments described here, therefore, provide critical evidence, in addition to double mutant analysis (Ang and Deng, 1994), that COP1 acts downstream of phyB.

The specificity of the effects of N282 expression on light-regulated development is supported by two lines of evidence. First, the phenotype of all the transgenic N282 lines is limited to the light control of seedling development, and little effect was detected on other developmental process and normal adult development. Second, both the expression of N282 and the cop1-4 mutation had almost no effect on the expression levels or induction of stress-or pathogen-responsive PR genes examined (FIG. 8). These results strongly suggest that photomorphogenic development is the process that is most sensitive to the modulation of COP1 activity. Taken together with the fact that COP1 activity is modulated by multiple photoreceptors (see above) and its nuclear localization is light regulated (von Arnim and Deng, 1994), our results support the conclusion that COP1 is specifically involved in a signaling cascade mediating light control of seedling development. However, our result cannot rule out the possibility that COP1 plays: a role in the developmental processes that were unaffected by N282 expression. Thus, it is formally possible that COP1 may also play roles in other developmental processes or that the activity of COP1 may be regulated by other cellular or external signals.

Implications for the Function of the COP1 N-Terminal Domains

In our opinion, there are at least three plausible mechanisms that could be responsible for the dominant negative phenotype caused by the expression of N282 (FIG. 9). These models assume that the N282 COP1 protein fragment interferes with the signaling processes of the wildtype COP1 protein directly. First, the N282 fragment may be able to interact with some factor or factors that are necessary for COP1 to exert its repressive influence on photomorphogenesis (FIG. 9B). Potential candidates include light signal transduction proteins or promoter targets of downstream genes, because the RING-finger zinc-binding domain of COP1 may be able to bind DNA. In the, N282 transgenic plants, the high levels of . N282 protein may titrate out such factors, reducing their availability to the endogenous full-length COP1 protein. This would result in a decrease in the ability of the wildtype COP1 protein to inhibit photomorphogenesis, and it would explain the partially de-etiolated phenotype of the N282 transgenic seedlings in darkness as well as their increased sensitivity to a variety of light signals. In this case, it is implied that N282 contains the protein motifs necessary for mediating those proposed interactions. Second, N282 has a domain mediating COP1—COP1 interaction, and the presence of N282 in the cells will lead to a non-productive N282-COP1 association (FIG. 9A). Although we have yet to analyze these interactions in Arabidopsis, the ability of N282 to interact with COP1 in yeast is consistent with this possibility. The third mechanism is a combination of the two mentioned above. Our preliminary results seem to be consistent with this combined option, because it appears that N282 contains distinct motifs that mediate interactions with COP1 and other novel cellular proteins (K. U. Torii and X. W. Deng, unpublished data). The proposal that N282 interferes with possible in vivo protein-protein interactions is consistent with the observation that the level of N282 is important in achieving the dominant-negative phenotype. For example, the degree of inhibition of hypocotyl elongation in different N282 lines correlates with the abundance of N282 protein. It is also consistent with the observation that the cop1-4 mutation results in the production of a very low level of N282 protein, and it behaves as a completely recessive mutation (McNellis et al., 1994a).

In summary, it seems clear that N282 of COP1 are involved in protein-protein or protein-nucleic acid interactions that are essential for the light control of seedling development by COP1. It will be necessary to assess the function of the zinc-binding and coiled-coil domains of COP1 separately, because both of these domains were included in the N282 fragment. This may be done in a similar manner by using deletions of specific domains of the protein or expression of isolated domains. It will be also interesting to exam the functionality of N282 in a null cop1 mutant background. This is because our current interpretations are based on the assumption that the phenotype of N282 expression is a result of its interference with the endogenous COP1 function. It is formally possible that high levels of N282 itself may cause the observed phenotypic effects independent of the presence of wildtype COP1. Isolation of interacting partners of COP1 may reveal the mode of action of COP1 in regulating Arabidopsis development.

EXAMPLES

Materials and Methods

Plant Transformation

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as resistance to an insect pest, and to introduce these genes into already useful varieties of plants. Once the foreign genes have been introduced into a plant, that plant can than be used in conventional plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site-specific modifications in endogenous genes and thus inherited or acquired mutations may be corrected, and/or novel alterations may be engineered into the genome.

Homologous recombination and site-directed integration in plants are discussed in U.S. Pat. Nos. 5,451,513, 5,501, 967 and 5,527,695.

Transgenes

Genes successfully introduced into plants using recombinant DNA methodologies include, but are not limited to, those coding for the following traits: seed storage proteins, including modified 7S legume seed storage proteins (U.S. Pat. Nos. 5,508,468, 5,559,223 and 5,576,203); herbicide tolerance or resistance (U.S. Pat. Nos. 5,498,544 and 5,554, 798; Powell et al., *Science* 232:738–743 (1986); Kaniewski et al., *Bio/Tech.* 8:750–754 (1990); Day et al., *Proc. Natl. Acad. Sci. USA* 88:6721–6725 (1991)); phytase (U.S. Pat. No. 5,593,963); resistance to bacterial, fungal, nematode and insect pests, including resistance to the lepidoptera insects conferred by the Bt gene (U.S. Pat. Nos. 5,597,945 and 5,597,946; Hilder et al., *Nature* 330:160–163; Johnson et al., *Proc. Natl. Acad. Sci. USA*, 86:9871–9875 (1989); Perlak et al., *Bio/Tech.* 8:939–943 (1990)); lectins (U.S. Pat. No. 5,276,269); and flower color (Meyer et al., *Nature* 330:677–678 (1987); Napoli et al., *Plant Cell* 2:279–289 (1990); van der Krol et al., *Plant Cell* 2:291–299 (1990)). Expression Units to Express Exogenous DNA in a Plant As provided above, several embodiments of the present invention employ expression units (or expression vectors or systems) to express an exogenously supplied nucleic acid sequence, such as the sequence coding for N282 protein in a plant. Methods for generating expression units/systems/vectors for use in plants are well known in the art and can readily be adapted for use in expressing the N282 protein in a plant cell. A skilled artisan car readily use any appropriate plant/vector/expression system in the present methods following the outline provided herein.

The expression control elements used to regulate the expression of the protein can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumafacians*. Alternatively, plant viral promoters can also be used, such as the cauliflower mosaic virus 35S promoter to control gene expression in a plant. Lastly, plant promoters such as prolifera promoter, fruit-specific promoters, Ap3 promoter, heat shock promoters, seed-specific promoters, etc. can also be used. The most preferred promoters will be most active in seedlings.

Either a constitutive promoter (such as the CaMV or Nos promoter), an organ-specific promoter (such as the E8 promoter from tomato) or an inducible promoter is typically ligated to the protein or antisense encoding region using standard techniques known in the art. The expression unit may be further optimized by employing supplemental elements such as transcription terminators and/or enhancer elements.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a preexisting vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the Agrobacterium octopine synthase signal (Gielen et al, *EMBO J* 3: 835–846 (1984)) or the nopaline synthase signal (Depicker et al., *Mol. and Appl. Genet.* 1: 561–573 (1982)).

The resulting expression unit is ligated into or otherwise constructed to be included in a vector which is appropriate for higher plant transformation. The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, in the case of Agrobacterium transformations, T-DNA sequences will also be included for subsequent transfer to plant chromosomes.

Methods to produce antisense encodiny vectors

Methods for inhibiting expression in plants using antisense constructs, including generation of antisense sequences in situ are described, for example, in U.S. Pat. Nos. 5,107,065 and 5,254,800.

Other methods that can be used to inhibit expression of an endogenous gene in a plant may also be used in the present methods. For example, formation of a triple helix at an essential region of a duplex gene serves this purpose. The triplex code, permitting design of the proper single stranded participant is also known in the art. (See H. E. Moser, et al., *Science* 238: 645–650 (1987) and M. Cooney, et al., *Science* 241: 456–459 (1988)). Regions in the control sequences containing stretches of purine bases are particularly attractive targets. Triple helix formation along with photo-crosslinking is described, e.g., in D. Praseuth, et al, *Proc. Nat'l Acad. Sci. USA* 85: 1,349–1,353 (1988).

Transformation Methods

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and Agrobacterium-mediated transformation (see, e.g., U.S. Pat. Nos. 5,405,765, 5,472,869, 5,538,877, 5,538,880, 5,550,318, 5,641,664, 5,736,369 and 5,736369; Watson et al., *Recombinant DNA*, Scientific American Books (1992); Hinchee et al., *Bio/Tech.* 6:915–922 (1988); McCabe el al., *Bio/Tech.* 6:923–926 (1988); Toriyama et al., *Bio/Tech.* 6:1072–1074 (1988); Fromm et al., *Bio/Tech.* 8:833–839 (1990); Mullins et al., *Bio/Tech.* 8:833–839 (1990); and, Raineri et al., *Bio/Tech.* 8:33–38 (1990).

Breeding Methods

1. Open-Pollinated Populations; The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are-crossed either naturally (e.g., by wind) or by hand or by bees (commonly *Apis mellifera* L. or *Megachile rotundata* F.) with plants from other populations Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population which is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Qugntitative Genetics in Maize Breeding*, Iowa State University Press (1981); and, Jensen, *Plant Breeding Methodology*, John Wiley & Sons, Inc. (1988).

2. Mass Selection. In mass selection, desirable individual plants are chosen,. harvested, and the seed composited without progeny testing to produce the following generation. Since selection is based on the maternal parent only, and their is no control over pollination, mass selection amounts to a form of random mating with selection. As stated above, the purpose of mass selection is to increase the proportion of superior genotypes in the population.

3. Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (Vicia) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic vary widely. In practice, numbers of parental lines range from 10 to several hundred, with 100–200 being the average. Broad based synthetics formed from 100 or more clones would be expected to be more stable during seed multiplication than narrow based synthetics.

4. Hybrids. A hybrid is an individual plant resulting from a cross between parents of differing genotypes. Commercial hybrids are now used extensively in many crops, including corn (maize), sorghum, sugarbeet, sunflower and broccoli. Hybrids can be formed a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an outbreeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity which results in increased vigor of growth, survival, and fertility of hybrids as compared with the parental lines which were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, Commercial Hybrid Seed Production 8:161–176, In *Hybridization of Corp Plants*, supra.

Construction of Expression Cassettes. Stable Transformation and Growth Conditions.

The cop1-4 mutant is an *Arabidopsis thaliana* Columbia ecotype (Deng and Quail, 1992a). For the N282 construct, the start codon of the cloned cop1-4 mutant cDNA was mutated to create an NcoI site, and the N-terminal half of the cop1-4 cDNA (McNellis et al., 1994a) was excised as an NcoI-HincII fragment and used to replace the β-glucuronidase (GUS) gene in the pRTL2-GUS plasmid (Restreppo et al., 1990). To excise the GUS gene from pRTL2-GUS, the plasmid was cut with BamHI, blunt ended with the Klenow fragment of DNA polyrnerase 1 and then cut with NcoI. This produced the N282 COP1 fragment encoding the N-terminal 282 amino acids of COP1. The nucleotide and amino acid sequences of N282 are provided in FIG. 11.

The resulted N282 expression construct was ligated as HindIII fragments into the binary plant transformation vector pBIN19 (Bevan, 1984). *Arabidopsis plants of the Nossen ecotype (No-0)* ecotype were transformed according to a published procedure (McNellis et al., 1994b). All wildtype plant were thus the Nossen ecotype unless specified otherwise. Plant germination and growth conditions and light sources were identical to those described previously (McNellis et al., 1994b).

Protein Gel Blot and RNA Gel Blot Analysis.

Protein immunoblot analysis was performed exactly as described previously (McNellis et al., 1994a). For RNA analysis, wildtype and N282 (L2) overexpressing seedlings were grown in darkness or cycling white light for 6 days. The seedlings were then harvested in either darkness or room light, and total RNA was isolated (Deng et al., 1991; Torii et al., 1996). Equal amounts of RNA (2.5 μg per lane) were subjected to RNA gel blot hybridization analysis as described previously (Torii et al., 1996). The RNA gel blots were hybridized with probes for light-regulated genes, and later reprobed with a probe for the 18S rRNA, which served as an equal loading control (Denget al., 1991).

For the pathogenesis-related (PR) genes, the seedlings were grown in GM medium (McNellis et al., 1994b) with or without 0.1 mM INA (2,6-dichloroisonicotinic acid) for 10 days under 16 hrs of white light and 8hrs of darkness. Whole seedlings were harvested and used for RNA extraction. Equal amounts of total RNA (20 μg per lane) were used for RNA blot analysis.

Light and Electron Microscopy.

The light and scanning electron microscopy procedures were performed as described previously (Hou et al., 1993). Transmission electron microscopy was performed as previously described (Wei et al., 1994a).

Yeast Two-Hybrid Assay

The pTA1-4, a pCR™ II clone (Invitrogen, San Diego, Calif.) with a cDNA insert corresponding to cop1-4 (McNellis et al. 1994a) was cut with BamHI and XhoI and inserted into a vector portion of pKS-COP1 (Deng et al. 1992) to generate pKS-N282. pKS-N282 was cleaved with EcoRI and cloned into pEG202 and pJG4-5 (Ausubel et al. 1994) to make in-frame fusions with LexA and an activation domain, respectively. The generated plasmids were designated as pEG-N282 and pJG-N282, respectively. To construct pJG-COP1, which contains the full-length COP1 fused to an activation domain, pKS-COP1 was cleaved with EcoRI and the released insert was cloned into an EcoRI digested pJG4–5 vector.

Yeast strain EGY48–0 (Ausubel et al. 1994) was transformed with combination of three plasmids; a bait (pEG-N282), a prey (pJG-N282 or pJG-COP1), and a reporter (pSH18-34) according to Chen et al. (1992). Colonies were selected on synthetic complete media without histidine, tryptophan, and uracil. The following combinations were transformed as controls:

pEG-N282, pJG4-5 (activation domain only); pSH18-34; pEG202 (LexA only), pJG-N282, and pSH18-34. Expression of N282 and COP1 in yeast transformants was confirmed by protein gel blots using anti-COP1 and/or anti-LexA antibodies (data not shown).

A β-galactosidase activity assay oft he transformants was performed using o-nitrophenyl-β-D-galactoside according to Guarente (1983) with the following modifications., Yeast strains were cultured in liquid media supplemented with 2% (w/v) glucose overnight, and then aliquots were transferred to media supplemented with 2% (w/v) galactose and 1% (w/v) raffinose to induce the expression of preys which are under the control of GAL1 promoter (Ausubel et al., 1994). Relative activity units were calculated according to Ausubel et al. (1994).

Example 1

Production of Stably Transformed Arabidopsis Transgenic Lines

Figure 1:
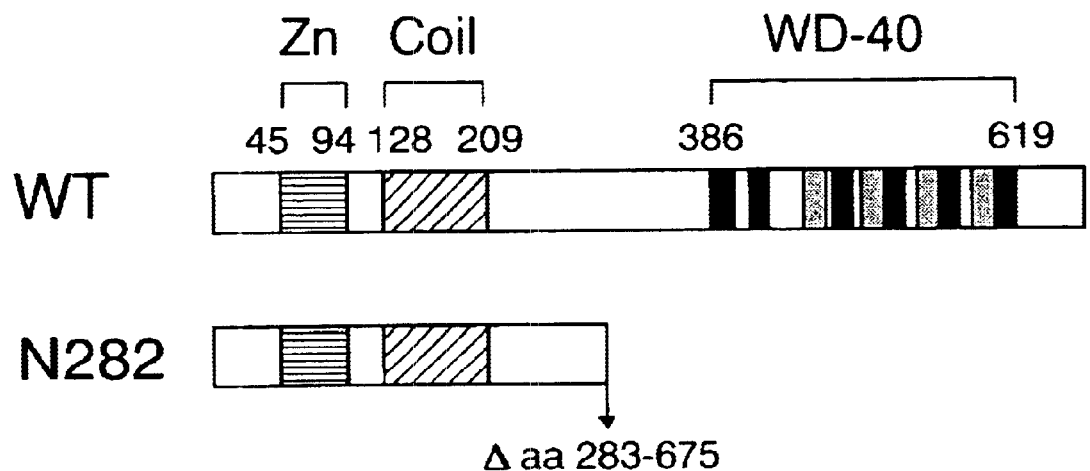
FIG. 1. Summary of N282 COP1 Protein Fragment and its Expression in Transgenic Plants.
  (A) The N282 is shown in comparison with the wildtype COP1 protein (675 amino acids), with the locations of the RING-finger zinc-binding (Zn), coiled-coil (Coil), and the $G_\beta$ domains. The $G_\beta$ domain is made up of multiple repeats of the WD-40 motif, which consists of A (dotted rectangles) and B (black rectangles) subrepeats. WT, wildtype; aa, amino acids.
  (B) Protein blots of two representative N282 transgenic lines in comparison to wildtype. Equal amounts of total protein extracts (about 10 µg) were analyzed. The N282 protein (33 kD, marked by arrows) in the transgenic lines accumulated to a level about 8 to 10 fold higher than the level of the wildtype full-length COP1 protein (76 kD). Note that the N282 transgenic lines also accumulated two other bands at around 60 and 70 kD, the identity of which are not clear. Molecular mass markers (in kD) are indicated at right.
Figure 1:
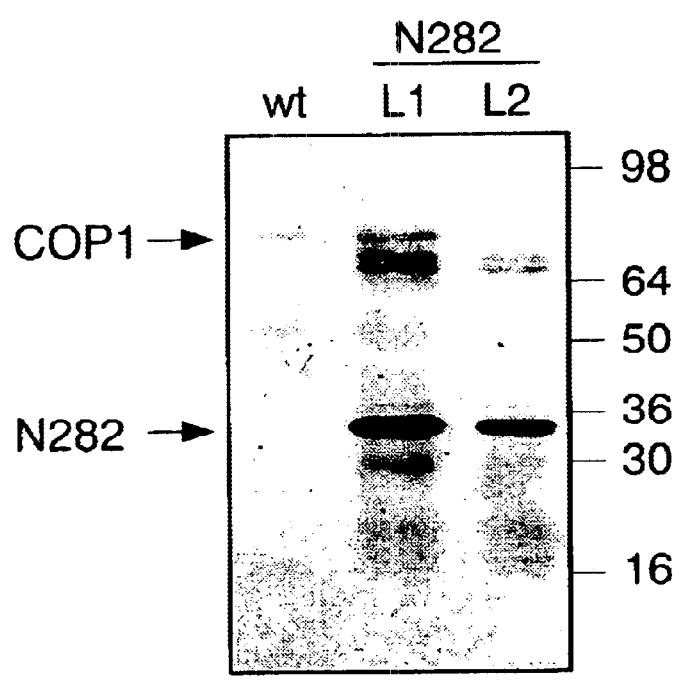

A cDNA fragments encoding the N-termninal 282 amino acids (N282) of COP1 was placed under the control of the strong cauliflower mosaic virus 35S RNA promoter for overexpression. The construct included proper start and stop codons as well as a viral translational leader sequence to improve the efficiency of translation (see Methods). FIG. 1A shows a schematic diagram of the predicted N282 in comparison to wildtype COP1. N282 is a truncated COP1 protein with predicted molecular masse of 33 , kD. The construct was stably introduced into Arabidopsis by Agrobacterium-mediated transformation. A total of 14 independent transgenic lines with the transgenes encoding N282 were generated and are summarized in Table 1.

TABLE 1

N282 Transgenic Line Summary

| Line | T-DNA Insertion Loci[a] | Hypocotyl Length[b] |
|---|---|---|
| UR-1[c] | 0 | Wildtype[d] |
| L1 | 1 | Very short[e] |
| L2 | 1 | Very short |
| L3 | 1 | Short[f] |
| L4 | 1 | Very short |
| L5 | 1 | Very short |
| L6 | 1 | Very short |
| L7 | 1 | Short |
| L8 | 1 | Short |
| L9 | 1 | Short |
| L10 | 1 | Very short |
| L11 | 2 | Very short |
| L12 | 2 | Very short |
| L13 | 2 | Very short |
| L14 | 3+[g] | Wildtype |

[a]The number of insertion loci was determined by kanamycin resistance segregation in the $T_1$ generation, as described in Methods.
[b]Hypocotyl length after 5 days of growth in cycling white light conditions, as described in Methods.
[c]UR-1, an untransformed line regenerated during the transformation process.
[d]The average wildtype hypocotyl length was 2.5 mm ± 0.5 mm.
[e]"Very short" indicates that the average hypocotyl length was <1 mm.
[f]"Short" indicates that the average hypocotyl length was >1 mm but <2.0 mm.
[g]Fifty-eight $T_1$ seeds were screened from this line, and all of them were found to be kanamycin resistant, indicating the presence of at least three insertion loci.

Among the 14 transgenic lines, 10 of the lines (L1 to L10) contained single T-DNA insertion locus, three of the lines (L11–L13) contained two insertion loci, and one line (L14) contained at least three insertion loci. Homozygous plants were isolated from all 10 lines with single T-DNA insertions. Immunoblot analysis of seedlings from these homozygous lines indicated that they all accumulated copious quantities of the 33 kD N282 protein. FIG. 1B shows a representative immunoblot for the two representative lines L1 and L2. The amount of N282 protein accumulating in the different lines varied from 8 to l0 times as strong as the intensity of the wildtype COP1 protein signal. The nature of the doublet at about 64 to 70 kD in the transgenic lines is not clear, although the bands appear to be specific to the transgenic lines. It is important to note that the level of the endogenous, full-length COP1 protein in all transgenic lines examined appeared to be unaltered. Therefore, the phenotypes are due to the overexpression of N282 rather than suppression of the endogenous wildtype COP1 gene expression.

Example 2

Figure 2:
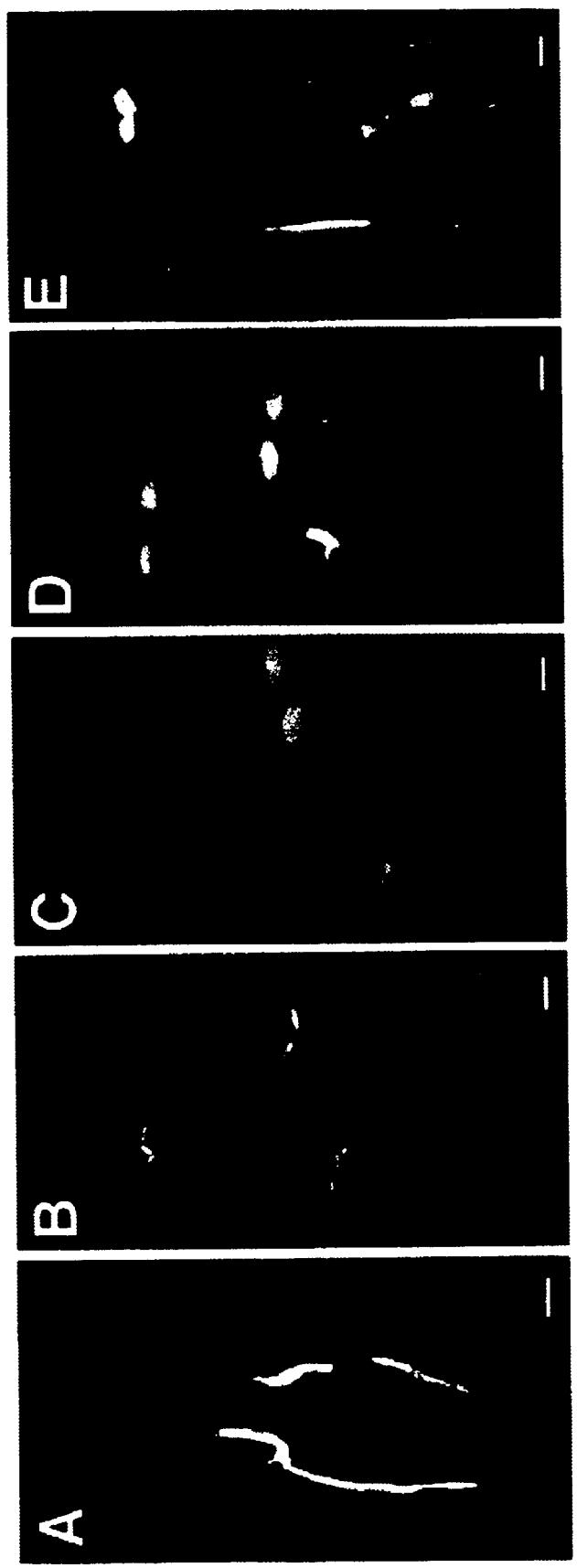
FIG. 2. Morphogenetic Comparison of Wildtype (WT) and N282 Seedlings (L1) Grown Under Various Light Conditions.
  (A) A wildtype and an N282 seedling grown for 5 days in cycling (16 hrs light/8 hrs dark) white light.
  (B) A wildtype and an N282 seedling grown for 5 days in continuous far-red light.
  (C) A wildtype and an N282 seedling grown for 5 days in continuous red light.
  (D) A wildtype and an N282 seedling grown for 5 days in continuous blue light.
  (E) A wildtype and an N282 seedling grown for 5 days in complete darkness.

Transgenic Arabidopsis Lines Accumulating the N282 Protein Display a Short Hypocotyl Phenotype in White Light When seeds from the N282 primary transformants were germinated under normal long-day white light conditions, it became immediately obvious that 13 of the 14 lines were segregating an obviously short hypocotyl phenotype (Table 1, FIGS. 2A and 3A). The strength of the short hypocotyl phenotype varied among the lines. The one line that showed a normal, wildtype hypocotyl elongation (about 2.5 mm) in white light was L14, a line with three or more T-DNA insertion loci. The reasons for this exception are not currently known. The other lines fell into two basic classes with regard to hypocotyl length (Table 1). Those with the more extreme phenotype were categorized as very short, having an average hypocotyl length of no more than 1 mm in cycling white light. Nine of the N282 lines displayed a very short hypocotyl phenotype, and they were all very similar in the degree of hypocotyl length inhibition. The length of the hypocotyl in those light-grown seedlings are essentially identical to that of the light-grown cop1-1 and cop1-4 mutants (FIG. 3A). Four of the N282 lines were classified in the short hypocotyl group. These lines had average hypocotyl lengths of greater than 1.0 mm, but less than 2.0 mm. There appeared to be a general correlation between the degree of hypocotyl shortening and the level of N282 accumulation (data not shown). The short hypocotyl phenotype in the N282 lines always segregated with the T-DNA (see following sections). This, taken together with the fact that 13 out of 14 N282 transgenic lines displayed a short hypocotyl phenotype, suggests that the short hypocotyl phenotype was caused by the accumulation of N282 protein.

Example 3

High-Level Accumulation of the N282 Protein Causes Hypersensitivity to Far-Red, Red, and Blue Light To investigate the nature of the photoreceptors involved in the hypersensitivity of the N282 seedlings to light signals, N282 seedlings from different N282 lines were examined in detail under far-red, red, and blue light conditions designed to primarily stimulate the photoreceptors phyA, phyB, and CRY1, respectively (FIGS. 2B, 2C, and 2D). FIG. 4A shows the average hypocotyl lengths for wildtype seedlings and seedlings from three representative N282 lines grown in continuous far-red, red, and blue light. Under all three light conditions, lines L1 and L2 have an extremely short average hypocotyl (about 1 mm), whereas line L3 has an intermediate hypocotyl length. These results correlated well with the severity of the phenotype observed for these lines under white light growth conditions (see Table 1). Again, the hypocotyl length of the severe transgenic lines are very much similar to that of the cop1 mutants under the same conditions (FIG. 4A), with the only minor difference in red light. While the cop1-4 seedlings under red light have very uniformly short hypocotyls about 1 mm, the hypocotyl lengths of some transgenic lines (such as L1) are slightly more variable as reflected by the large error bar (FIG. 4A). The hypersensitivity of the N282 transgenic lines to far-red, red, and blue light mimics that caused by overexpression of Arabidopsis PHYA (Boylan and Quail, 1991), PHYB (Wagner et al., 1991), or CRY1 (Lin et al., 1995) photoreceptors, respectively. This implies that the overexpression of N282 resulted in hypersensitivity to light stimulation mediated by at least three independent photoreceptors. It should be pointed out that the hypersensitivity to blue light is complicated by the fact that phytochromes also absorb blue light, and it cannot be ruled out that an increase in responsiveness to PhyB stimulation by blue light contributes to the short hypocotyl phenotype of the N282 lines in blue light. However, although the N282 plants had a similar phenotype to that of PhyB overexpressers in red light, they had a stronger phenotype in blue light than the PhyB overexpressers (Wagner et al., 1991). This suggests that hypersensitivity to blue light photoreceptor stimulation must play a role in causing the phenotype of the N282 lines in blue light.

It is worth mentioning that although COP1 was placed downstream of phyB based on double mutant analysis, our previous full-length COP1 overexpression analysis failed to show any measurable effect on PhyB-mediated red light inhibition of seedling hypocotyl elongation (McNellis et al., 1994b). Therefore, the hypersensitivity of N282 lines to continuous red light provides clear evidence supporting the conclusion that COP1 also functions downstream of PhyB in addition to phyA and CRY1.

Example 4

The Short Hypocotyl Phenotype Observed in the N282 Transgenic Arabidopsis Lines is Genetically Dominant To establish the causal relation of N282 expression and the hypocotyl phenotype, the progeny of a representative plant heterozygous for a single T-DNA insertion locus of the N282 transgene (line L2) were analyzed for phenotypic segregation in far-red, red, and blue light conditions and the results are summarized in FIG. 4B. In each case, the seedlings segregated into two clearly distinct phenotypic classes: very short (about 1 mm) and wildtype. The short hypocotyl phenotype always cosegregated with the T-DNA: all seedlings with short hypocotyls were positive for the T-DNA resistance marker and all wildtype-like siblings lacked the T-DNA locus (data not shown). In far-red light, the ratio of the number of short to the number of long seedlings was about three to one, indicating that the N282 transgene had a completely dominant effect in far-red light (P>0.1). Similar results were obtained in red light (P>0.9) and blue (P>0.99) light, indicating that the N282 transgene had a dominant effect under those conditions as well.

Example 5

Accumulation of the N282 Protein Causes Partial Photomorphogenic Development and Cell Differentiation in Darkness The dramatic short hypocotyl phenotype of the N282 transgenic lines under different light regimens is reminiscent of the phenotype of weak cop1 mutants (Deng and Quail, 1992). This prompted us to investigate whether production of the N282 protein could cause constitutive photomorphogenic development in the dark. As shown in FIG. 2E, dark-grown seedlings expressing N282 do indeed have open and expanded cotyledons, a characteristic of de-etiolation or photomorphogenic development. Scanning electron microscopy examination of the cotyledon surface cells (FIGS. 5A to 5D) indicated that dark-grown N282 seedlings have epidermal cell expansion and differentiation patterns similar to the cotyledons of light-grown seedlings, including mature stomatal structures. However, the de-etiolation effects of N282 expression seem to be restricted to cotyledon development, because dark-grown N282 seedlings did not display significant inhibition of hypocotyl elongation relative to the wildtype, contrasting to the dark-grown cop1 mutants (FIG. 3B). It is important to note that only seedlings from the N282 lines that were classified as being very short (Table 1) exhibited photomorphogenic development in the dark, whereas those N282 lines with weaker light-grown phenotypes resembled wildtype seedlings when grown in the dark (data not shown). This implied that a high threshold level of available N282 was required to cause constitutive photomorphogenic cotyledon development in the dark. This may also imply that photomorphogenic hypocotyl development in the dark would require an even higher threshold level of N282.

Example 6

Expression of N282 Results in Partial Chloroplast Development and Activation of Normally Light-Inducible Genes in the Absence of Light To determine whether the de-etiolated phenotype of the N282 lines included any alterations in plastid development and gene expression, plastids of dark-grown N282 seedlings were examined by transmission electron microscopy, and the dark expression levels of light-regulated genes in the N282 lines were determined by RNA gel blot analysis. As shown in FIG. 6, the plastids of dark-grown N282 seedlings have a very similar morphology to those of dark-grown cop1-1 and cop1-4 mutants (Deng et al., 1991; Deng and Quail, 1992). The plastids of dark-grown N282 seedlings in general do not have the prolamellar bodies characteristic of etioplasts, but instead have slightly more extensive thylakoid membrane structures that are similar to those found in immature chloroplasts. Therefore, N282 expression prevented etioplast development and promoted partial chloroplast development.

To examine the effects of N282 expression on light-regulated gene expression, mRNA levels of three representative genes (cab, the nuclear genes encoding the chlorophyll a/b binding protein; rbcS, the nuclear genes encoding the small subunit of ribulose-1,5-bisphosphate carboxylase; and psbA, the plastid gene encoding the 32 kD protein of the photosystem II reaction center) were examined in 6-day-old dark and light grown seedlings. As shown in FIG. 7, RNA blot gel analysis indicated that all of the genes examined exhibiting elevated levels of mRNA in dark-grown N282 seedlings in comparison to wildtype, although the dark mRNA level was not as high as the level observed in light-grown seedlings. This elevated dark expression of genes that are normally only highly expressed in the light is very similar to that caused by the weak cop1-4 mutation. Therefore, expression of N282 not only induced photomoiphogenic seedling development, but also led to abnormal plastid development and failure to repress light-inducible genes in complete darkness.

Example 7

Both N282 Accumulation and COP1-4 Mutation Have Minimal Defect in Pathogenesis-Related Gene Expression or Induction To test the specificity of the effects of N282 expression on light-regulated development and gene expression, we examined whether the N282 transgenic lines exhibited any altered expression of the Arabidopsis pathogenesis-related (PR) genes (Uknes et al., 1992). The PR genes are repressed in normal wildtype plants, but can be induced to high levels by a variety of signals including pathogen infection, elicitors, salicylic acid, UV-B stress, and synthetic compounds such as 2,6-dichloroisonicotinic acid (INA) (Uknes et al., 1992; Chen et al., 1993; Cao et al., 1994; Green and Fluhr, 1995). We anticipated that if COP1 were a global regulator affecting overall gene regulation in plants, then the N282 lines and cop1 mutants might exhibit an altered pattern of PR gene expression. As FIG. 8 shows, the expression patterns of two PR genes, PR1, and PR2 (Ukness et al., 1992), are very similar in N282 transgenic, COP1-4 mutant, and wildtype plants. In the absence INA, an agent that induces systemic acquired resistance and PR gene expression, the two PR genes were completely repressed and no measurable mRNA accumulation was detected. This undetectable PR, gene expression is observed in both light-(FIG. 8) and dark-grown (data not shown) wildtype and mutant seedlings. While in the presence of 0.1 mM INA, the mRNAs of the two PR genes accumulated to high levels in wildtype, N282 expressing, and cop1-4 mutant seedlings. The expression of PR genes in the N282 or cop1-4 mutant lines are slightly higher than that of the wildtype in the presence of INA. However, this difference is rather minor and therefore we concluded that neither N282 expression nor the cop1-4 mutation had a significant effect on the expression and inducibility of the two Arabidopsis PR genes examined.

Example 8

N282 Interacts With Both Full-Length COP1 and N282 Itself in Yeast

All the phenotypic characteristics of the N282 expressing lines indicated that the presence of N282 somehow interferes with or blocks the normal function of the endogenous wildtype COP1. At least two general mechanisms could potentially account for this effect. As shown in FIG. 9A, one possibility is that N282 interacts with wildtype COP1 to form an unproductive association, which leads to a dominant phenotype. It is also equally possible that N282 may interact with and titrate out the normal downstream targets of COP1 action, thus preventing the wildtype COP1 protein from performing its function normally (FIG. 9B). As a first step to gain insight into the possible mechanism involved, we tested whether N282 indeed has the capacity to interact with COP1 using the yeast two-hybrid assay (Gyuris et al., 1993). As shown in FIGS. 10A, 10B, and 10C, the two proteins of interest were fused to either the LexA DNA binding domain (bait) or the yeast transcription activation domain (prey). If the bait and prey interact, the reporter lacZ gene, which contains the LexA binding site in its promoter, will be activated. The results of this assay clearly suggested that N282 is indeed able to interact with full-length COP1 in yeast. Most strikingly, the interaction between two N282 molecules was even stronger than that between N282 and full-length COP1. Because N282 does not interact with either the LexA or the activation domain alone, our results clearly indicate that N282 protein contains the domains responsible for intermolecular interaction of COP1. The reason for a stronger interaction between the N282 molecules than that between N282 and COP1 is not clear. However, one possible explanation is that the presence of the C-terminal half of the protein may somehow weaken the protein-protein interaction through steric hindrance or regulatory inhibition of the COP1 intermolecular interaction. It is also possible that the full-length COP1 in yeast was not properly expressed or subcellularly localized.

Example 9

Production of Stably Transformed Transgenic Tomato Lines Using the Arabidopsis N282 Sequence As discussed above, Frances et al. (1998) have established that tomato plants inherently contain a homologue of the Arabadopsis COP1 gene, designated TCOP1.

The Arabidopsis N282 expression construct is ligated as HindIII fragments into the binary plant transformation vector pBIN19 as set forth in the Materials and Methods. Tomato plants (*Lycopersicon esculentum*, var. Better Boy) are transformed with the resultant vector according to published procedures (see, e.g.; McGurl et al., 1994, *Proc. Natl. Acad. Sci. USA* 91 (21):9799–9802; McGarvey et al., 1995, *Biotechnology* 13(13):1484–1487).

Seedlings are evaluated using plant germination, growth conditions and light sources described previously (McNellis et al., 1994b). Protein immunoblot analysis is performed as described previously (McNellis et al., 1994a) and as set forth above in the Materials and Methods.

Transformed tomato seedlings contain both the wildtype TCOP1 gene and the transgene coding for the N282 Arabadopsis protein. The transgenic tomato seedlings have shorter, more vigorous stems and greener, more developed leaves when compared to non-transfornmed Big Boy tomato seedlings grown under the same low light conditions. When grown to maturity under the same environmental conditions, the transgenic and non-transgenic (i.e., wildtype) tomato plants are not significantly different for total above-ground shoot growth or for yield of tomato fruits (botanically a berry).

Example 10

Production of Transformed Tomato Plants Using Conventional Plant Breeding

The transgenic Big Boy tomato plants produced in Example 9 are sexually crossed to non-transgenic Big Boy tomato plants (or another line, cultivar or variety of tomato plants) and the resultant seed is harvested. The harvested seed is planted and the seedlings are grown under low light conditions and selection is made for transformed seedlings. The transfornmed seedlings are grown to maturity and the resultant selfed seed is harvested and bulked to produce bulked transgenic seed for planting as a tomato crop plant.

Alternatively, the mature transformed plants are crossed to a different tomato line (a sister line or a different variety) to produce hybrid seed. The resultant hybrid seed is bulked and used to produce a hybrid tomato crop.

As discussed above in the Materials and Methods, numerous variations on these breeding schemes are possible. For example, the originally obtained transformed seedlings may be selfed for one or several generations before being used for the production of either selfed or hybrid seed production. For a discussion of, tomato production methods, see Langer

Example 11

Production of Stably Transformed Transgenic Rice Lines Arabidopsis N282 Sequence As discussed above, Tsuge et al. (1998) have established that rice plants inherently contain a homologue of the Arabidopsis COP1 gene.

The Arabidopsis N282 expression construct is ligated as HindIII fragments into the binary plant transformation vector pBIN19 as set forth in the Materials and Methods. Rice plants (*Oryza sativa* cv. Taipei 309) are transformed with the resultant vector according to published procedures (see, e.g., McElroy et al., 1991, *Plant Cell* 3(11):1155–1165; Nakayama et al., 1995, *Plant Mol. Biol.* 27(1):17–26; Su et al., 1998, *Plant Physiol.* 117(3):913–922; Cornejo et al., 1993, *Plant Mol. Biol.* 23(3):567–5811; Xu et al., 1993, *Plant Mol. Biol.* 22(4):573–588).

Seedlings are evaulated using plant germination, growth conditions and light sources described previously (McNellis et al., 1994b). Protein immunoblot analysis is performed as described previously (McNellis et al., 1994a) and as set forth above in the Materials and Methods.

Transformed rice seedlings contain both the wildtype rice COP1 gene and the transgene coding for the N282 Arabadopsis protein. The transgenic rice seedlings have shorter, more vigorous stems and greener, more developed leaves when compared to non-transformed rice seedlings grown under the same low light condtions. When grown to maturity under the same environemental conditions, the transgenic and non-transgenic (i.e., wildtype) rice plants are not significantly different for total above-ground shoot growth or for grain yield.

Example 12

Production of Transformed Rice Plants Using Conventional Plant Breeding

The transgenic rice plants produced in Example 11 are sexually crossed to non-transgenic rice plants (or another line, cultivar or variety of rice plants) and the resultant seed is harvested. The harvested seed is planted and the seedlings are grown under low light conditions and selection is made for transformed seedlings. The transformed seedlings are grown to maturity and the resultant selfed seed is harvested and bulked to produce bulked transgenic seed for planting as a rice crop plant.

Alternatively, the mature transformed plants are crossed to a different rice line (a sister line or a different variety) to produce hybrid seed. The resultant hybrid seed is bulked and used to produce a hybrid rice crop.

As discussed above in the Materials and Methods, numerous variations on these breeding schemes are possible. For example, the originally obtained transformed seedlings may be selfed for one or several generations before being used for the production of either selfed or hybrid seed production. For a discussion of rice production methods, see Langer et al., 1991, Agricultural Plants, Second Edition, Cambridge University Press and Coffman et al., 1980, Chapter 36, In Hybridization of Crop Plants, The American Society of Agronomy, Inc., Madison, Wis.

Example 13

Production of Stably Transformed Transgenic Tomato Lines Using the N-terminal Sequence of the TCOP1 Gene As discussed above, Frances et al. (1998) have cloned from tomato a homologue of the Arabadopsis COP1 gene, designated TCOP1. The N-terminal 282 amino acids of the TCOP1 gene, or, alternatively, the fragment of the TCOP1 gene encoding the N-terminal half which contains both the Zn-binding motif and the putative coiled-coil domain, are introduced into a vector according to the methods described herein. The resultant vector is used to produce transformed tomato plants which are characterized and/or used as set forth in Examples 9 and 10.

Example 14

Production of Stably Transformed Transgenic Rice Lines Using the N-terminal Sequence of the Rice COP1 Gene As discussed above, Tsuge et al. (1998) have cloned from rice a homologue of the Arabadopsis COP1 gene. The N-terminal 282 amino acids of the rice COP1 gene, or, alternatively, the fragment of the rice COP1 gene encoding the N-terminal half which contains both the Zn-binding motif and the putative coiled-coil domain, are introduced into a vector according to the methods described herein. The resultant vector is used to produce transformed rice plants which are characterized and/or used as set forth in Examples 11 and 12.

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

All references, articles, texts and patents referred to above and below are hereby incorporated by reference in their entirety.

Ahmad, M. and Cashmore, A. R. (1993). The HY4 gene involved in blue light sensing in *Arabidopsis thaliana* encodes a protein with the characteristics of a blue light photoreceptor. *Nature* 366, 162–166.

Ang, L. -H. and Deng, X. -W. (1994). Regulatory hierarchy of photomorphogenic loci: allele-specific and light-dependent interaction between the HY5 and COP1 loci. *Plant Cell* 6, 613–628.

Ausubel, F. M., Brent, R., Kingston, R. E., Moore, D. D., Seidman, J. G., Smith, J. A., and Struhl, K. eds (1994). *Saccharomyces cerevisiae* In Current Protocols in Molecular Biology, Supplement. (New York: John Wiley & Sons).

Bevan, M. (1984). Binary Agrobacterium vectors for plant transformation. *Nucl. Acids Res.* 12, 8711–8721.

Boylan, M. T., and Quail, P. H. (1991). Phytochrome A overexpression inhibits hypocotyl elongation in transgenic Arabidopsis. *Proc. Natl. Acad. Sci. USA* 88, 10806–10810.

Cao, H., Bowling S. A., Gordon, A. S., and Dong, X. (1994). Characterization of an Arabidopsis mutant that is nonresponsive to inducers of systemic acquired resistance. *Plant Cell* 6, 158314 1592.

Castle, L. A. and Meinke, D. W. (1994). A FUSCA gene of Arabidopsis encodes a novel protein essential for plant development. *Plant Cell* 6, 25–41.

Chen, D.-C., Yang, B.-C., and Kuo, T.-T. (1992). One-step transformation of yeast in stationary phase. *Curr. Genet.* 21, 83–84.

Chen, Z., Silva, H., and Klessig, D. F. (1993). Active oxygen species in the induction of plant systemic acquired resistance by salicylic acid. *Science* 262, 1883–1886.

Chory, J. (1993). *Trends Genet.* 9, 167–172.

Dehesh, K., Franci, C., Parks, B. M., Seeley, K. A., Short, T. W., Tepperman, J. M. and Quail, P. H. (1993). Arabidopsis HY8 locus encodes phytochrome A. *Plant Cell* 5, 1081–1088.

Deng, X.-W., Caspar, T., and Quail, P. H. (1991) cop1: A regulatory locus involved in light-controlled development and gene expression in Arabidopsis. *Genes Dev.* 5, 1172–1182.

Deng, X.-W. and Quail, P. H. (1992a). Genetic and phenotypic characterization of cop1 mutants of *Arabidopsis thaliana*. *Plant J.* 2, 83–95.

Deng, X.-W., Matsui, M., Wei, N., Wagner, D., Chu, A. M., Feldmann, K. A. and Quail, P. H. (1992b). COP1, an Arabidopsis regulatory gene, encodes a protein with both a zinc-binding motif and a $G_\beta$ homologous domain. *Cell* 71, 791–801.

Frances, S., White, M. J., Edgerton, M. D., Jones, A. M., Elliott, R. C. and Thompson, W. F. (1992). Initial characterization of a pea mutant with light-independent photomorphogenesis. *The Plant Cell* 4(12), 1519–130.

Frances, S., Matsui, M., Kendrick, R. E., and Deng, X.-W. A tomato homologue of the Arabidopsis COP1 gene exhibits a novel pattern of expression. ESOP Programmne and Abstracts. European Symposium on Photomorhogenesis, Jul. 12–18, 1997.

Furuya, M. (1993). *Annu. Rev. Plant Physiol. Plant Mol. Biol.* 44, 617–645.

Gilmartin, P. M., Sarokin, L., Memelink, J., and Chua, N.-H. (1990). *Plant Cell* 2, 369–378.

Green, R., and Fluhr, R. (1995). UV-B-induced PR-1 accumulation is mediated by active oxygen species. *Plant Cell* 7, 203–212.

Guarente, L. (1983). Yeast promoters and lacZ fusions designed to study expression of cloned genes in yeast. *Methods Enzymol.* 101, 181–191.

Gyuris, J., Golemis, E., Chertkov, H., and Brent, R. (1993). Cdil, a human G1 and S phase protein phosphatase that associates with Cdk2. *Cell* 75, 791–803.

Hou, Y., von Arnim, A. G. and Deng, X.-W. (1993). A new class of Arabidopsis constitutive photomorphogenic genes involved in regulating cotyledon development. *Plant Cell* 5, 329–339.

Kaufman, L. (1993). *Plant Physiol.* 102, 333–337.

Kendrick, R E. and Kronenberg, G. H. M. (1994). Photomorphogenesis in plants. (Dordrecht: Kluwer Academic Publishers).

Koornneef, M., Rolff, E. and Spruit, C. J. P. (1980). Genetic control of light-inhibited hypocotyl elongation in *Arabidopsis thaliana* (L.) Heynh. *Z. Pflanzenphysiol.* 100, 147–160.

Kwok, S. F., Piekos, B., Miséra, S., and Deng, X.-W. (1996) A complement of ten essential and pleiotropic Arabidopsis genes are necessary for suppression of photomorphogenesis in darkness. *Plant Physiol.* 110, 731–742.

Lin, C.-T., Alimad, M., Gordon, D., and Cashmore, A. R. (1995). Expression of an Arabidopsis cryptochrome gene in transgenic tobacco results in hypersensitivity to blue, UV-A, and green light. *Proc. Natl. Acad. Sci. USA* 92, 8423–8427.

McCormac, A. C., Cherry, J. R., Hershey, H. P., Vierstra, R. D., and Smith, H. (1991). Photoresponses of transgernc tobacco plants expressing an oat phytoclirome gene. *Planta* 185, 162–170.

McCormac, A. C., Whitelam, G. C., Boylan, M. T., Quail, P. H., and Smith, H. (1992). Light-grown plants of transgenic tobacco expressing an introduced oat phytochrome A gene under the control of a constitutive viral promoter exhibit persistent growth inhibition by far-red light. *Planta* 188, 173–181.

McCormac, A. C., Wagner, D., Boylan, M. T., Quail, P. H., Smith, H., and Whitelam, G. C. (1993). Photoresponses of transgenic Arabidopsis seedlings expressing introduced phytochrome B-encoding cDNAs: Evidence that phytochrome A. and phytochrome B have distinct photoregulatory functions. *Plant J.* 4, 19–27.

McNellis, T. W., and Deng, X.-W. (1995). Light control of seedling morphogenetic pattern. *Plant Cell* 7, 1749–1761.

McNellis, T. W., von Arnim, A. G., Araki, T., Komeda, Y., Misera, S. and Deng, X.-W. (1994a). Genetic and molecular analysis of an allelic series of cop1 mutants suggests functional roles for the multiple protein domains. *Plant Cell* 6, 487–500.

McNellis, T. W., von Arnim, A. G., and Deng, X.-W. (1994b). Overexpression of Arabidopsis COP1 results in partial suppression of light mediated development: evidence for a light-inactivable repressor of photomorphogenesis. *Plant Cell* 6, 1391–1400.

Miséra, S., Muller, A. J., Weiland-Heidecker, U. and J ürgens, G. (1994). The FUSCA genes of Arabidopsis: Negative regulators of light responses. *Mol. Gen. Genet.* 244, 242–252.

Nagatani, A., Reed, R. W. and Chory, J. (1993). Isolation and initial characterization of Arabidopsis mutants that are deficient in phytochrome A. *Plant Physiol.* 102, 269–277.

Parks, B. M. and Quail, P. H. (1993). hy8, a new class of Arabidopsis long hypocotyl mutants deficient in functional phytochrome A. *Plant Cell* 5, 39–48.

Pepper, A., Delaney, T., Washburn, T., Pool, D., and Chory, J. (1994). DET1, a negative regulator of light-mediated development and gene expression in Arabidopsis encodes a novel nuclear-localized protein. *Cell* 78, 109–116.

Quail, P. H. (1991). *Annu. Rev. Genet.* 25, 389–409.

Reed, J. M., Nagpal, P., Poole, D. S., Furuya, M. and Chory, J. (1993). Mutations in the gene for the red/far red light receptor phytochrome B alter cell elongation and physiological responses throughout Arabidopsis development. *Plant Cell* 5, 147–157.

Restreppo, M. A., Freed, D. D., and Carrington, J. C. (1990). Nuclear transport of plant potyviral proteins. *Plant Cell* 2, 987–998.

Thompson, W. F., and White, M. J. (1991). *Annu. Rev Plant Physiol. Plant Mol. Biol.* 42, 423–466.

Tomohiko, T. Yoshizumi, T., Deng, X.-W., and Matsui, M. 1997. Isolation and characterization of Arabidopsis COP1 homologous gene in rice. ESOP Programme and Abstracts. European Symposium on Photomorhogenesis, Jul. 12–18, 1997.

Torii, K. U., Mitsukawa, N., Oosumi, T., Matsuura, Y., Yokoyama, R., Whittier, R. F., and Komeda, Y. (1996). The Arabidopsis ERECTA gene encodes a putative receptor protein kinase with extracellular leucine-rich repeats. *Plant Cell* 8, 735–746.

Uknes, S., Mauch-Mani, B., Moyer, M., Potter, S., Williams, S., Dincher, S., Chandler, D., Slusarenko, A., Ward, E., and Ryals J. (1992). Acquired resistance in Arabidopsis. *Plant Cell* 4, 645–656.

Vierstra, R. (1993). *Plant Physiol.* 103, 679–684.

von Arnim, A. G., and Deng, X.-W. (1993). RING-finger motif of *Arabidopsis thaliana* COP1 defines a new class of zinc-binding domain. *J. Biol. Chem.* 268, 19626–19631.

von Arnim, A. G. and Deng, X.-W. (1994). Light inactivation of Arabidopsis photomorphogenic COP1 involves a cell-specific regulation of its nucleo-cytoplasmic partitioning. *Cell* 79, 1035–1045.

Wagner, D., Teppermann, J. M., and Quail, P. H. (1991). Overexpression of phytochrome B induces a short hypocotyl phenotype in transgenic Arabidopsis. *Plant Cell* 3, 1275–1288.

Wei, N., Chamovitz, D. A., and Deng, X.-W. (1994) Arabidopsis COP9 is a component of a novel signaling complex mediating light control of development. *Cell* 78, 117–124.

Wester, L., Somers, D. E., Clack, T., and Sharrock, R. A. (1994). Transgenic complementation of the hy3 phytochrome B mutation and response to PHYB gene copy number in Arabidopsis. *Plant J.* 5, 261–272.

Whitelam, G. C., McCortnac, A. C., Boylan, M. T., and Quail, P. H. (1992). Photoresponses of Arabidopsis seedlings expressing an introduced oat phyA cDNA: persistence of etiolated plant type responses in light-grown plants. *Photochem. Photobiol.* 56, 617–621.

Whitelamn, G. C., Johnson; E., Peng, J., Carol, P., Anderson, M. L., Cowl, J. S. and Harberd, N. P. (1993). Phytochrome A null mutants of Arabidopsis display a wildtype phenotype in white light. *Plant Cell* 5, 757–768.

Zhao, L., W. Chunxia, Y. Zhu, J. Zhao, and Wu, X. (1998). Molecular cloning and sequencing of the cDNA of cop1 gene from *Pisum sativum*. *Biochimica et Biophysica Acta* 1395, 326–328.

---

What is claimed is:

1. An isolated nucleic acid comprising a nucleic acid sequence encoding the N-terminal 282 amino acids of a COP1 protein, wherein said isolated nucleic acid is operably linked to a promoter, and wherein said isolated nucleic acid does not encode the WD-40 domain of COP1 protein.

2. The isolated nucleic acid of claim 1, wherein the promoter is a constitutive promoter.

3. The isolated nucleic acid of claim 2, wherein the promoter is a CaMV promoter.

4. A host cell comprising the isolated nucleic acid of claim 1.

5. The host cell of claim 4 wherein the host cell is a plant cell.

6. The plant cell of claim 5, wherein the plant is selected from the group of plant genera consisting of Arabidopsis, Spinachia, Lycopersicon, Pisum and Oryza.

7. A plant comprising the plant cell of claim 5.

8. A vector comprising the isolated nucleic acid of claim 1.

9. A host cell comprising the vector of claim 8.

10. A method of producing a transformed plant cell comprising transforming a plant cell with a vector of claim 8, thereby producing a transformed plant cell.

11. A method of producing a regenerated transformed plant comprising:
   a) transforming a plant cell with a vector of claim 8, and
   b) regenerating a transformed plant from the transformed plant cell of step a).

12. A method of producing a transformed plant that expresses the N-terminal 282 amino acids of a COP1 protein comprising:
   a) transforming a plant cell with a vector of claim 8,
   b) regenerating a transformed plant from the transformed plant cell;
   c) sexually crossing the regenerated transformed plant with at least one other plant to produce seeds from the sexual cross;
   d) harvesting the resultant seeds;
   e) growing plants from the resultant seeds; and
   f) selecting a transformed plant that expresses the N-terminal 282 amino acids of a COP1 protein.

\* \* \* \* \*

SEQUENCE LISTING

```
<160> NUMBER OF SEQ ID NOS: 2

<210> SEQ ID NO 1
<211> LENGTH: 888
<212> TYPE: DNA
<213> ORGANISM: Arabidopsis thaliana
<220> FEATURE:
<221> NAME/KEY: CDS
<222> LOCATION: (43)..(888)
<223> OTHER INFORMATION: DNA sequence of COP1 gene in cop1-4 mutant

<400> SEQUENCE: 1
caaaaaccaa aatcacaatc gaagaaatct tttgaaagca aa atg gaa gag att          54
                                               Met Glu Glu Ile
                                                 1 tcg acg gat ccg gtt gtt cca gcg gtg aaa cct gac ccg aga aca tct       102
Ser Thr Asp Pro Val Val Pro Ala Val Lys Pro Asp Pro Arg Thr Ser
  5                  10                  15                  20 tca gtt ggt gaa ggt gct aat cgt cat gaa aat gac gac gga gga agc       150
Ser Val Gly Glu Gly Ala Asn Arg His Glu Asn Asp Asp Gly Gly Ser
             25                  30                  35 ggc ggt tct gag att gga gca ccg gat ctg gat aaa gac ttg ctt tgt       198
Gly Gly Ser Glu Ile Gly Ala Pro Asp Leu Asp Lys Asp Leu Leu Cys
         40                  45                  50 ccg att tgt atg cag att att aaa gat gct ttc ctc acg gct tgt ggt       246
Pro Ile Cys Met Gln Ile Ile Lys Asp Ala Phe Leu Thr Ala Cys Gly
     55                  60                  65 cat agt ttc tgc tat atg tgt atc atc aca cat ctt agg aac aag agt       294
His Ser Phe Cys Tyr Met Cys Ile Ile Thr His Leu Arg Asn Lys Ser
 70                  75                  80 gat tgt ccc tgt tgt agc caa cac ctc acc aat aat cag ctt tac cct       342
Asp Cys Pro Cys Cys Ser Gln His Leu Thr Asn Asn Gln Leu Tyr Pro
 85                  90                  95                 100 aat ttc ttg ctc gat aag cta ttg aag aaa act tca gct cgg cat gtg       390
Asn Phe Leu Leu Asp Lys Leu Leu Lys Lys Thr Ser Ala Arg His Val
                105                 110                 115 tca aaa act gca tcg ccc ttg gat cag ttt cgg gaa gca cta caa agg       438
Ser Lys Thr Ala Ser Pro Leu Asp Gln Phe Arg Glu Ala Leu Gln Arg
            120                 125                 130 ggt tgt gat gtg tca att aag gag gtt gat aat ctt ctg aca ctt ctt       486
Gly Cys Asp Val Ser Ile Lys Glu Val Asp Asn Leu Leu Thr Leu Leu
        135                 140                 145 gcg gaa agg aag aga aaa atg gaa cag gaa gaa gct gag agg aac atg       534
Ala Glu Arg Lys Arg Lys Met Glu Gln Glu Glu Ala Glu Arg Asn Met
```

-continued

| | |
|---|---|
| cag ata ctt ttg gac ttt ttg cat tgt cta agg aag caa aaa gtt gat<br>Gln Ile Leu Leu Asp Phe Leu His Cys Leu Arg Lys Gln Lys Val Asp<br>165                   170                         175                    180 | 582 |
| gaa cta aat gag gtg caa act gat ctc cag tat att aaa gaa gat ata<br>Glu Leu Asn Glu Val Gln Thr Asp Leu Gln Tyr Ile Lys Glu Asp Ile<br>                         185                         190                    195 | 630 |
| aat gcc gtt gag aga cat aga ata gat tta tac cga gct agg gac aga<br>Asn Ala Val Glu Arg His Arg Ile Asp Leu Tyr Arg Ala Arg Asp Arg<br>200                   205                       210 | 678 |
| tat tct gta aag ttg cgg atg ctc gga gat gat cca agc aca aga aat<br>Tyr Ser Val Lys Leu Arg Met Leu Gly Asp Asp Pro Ser Thr Arg Asn<br>        215                       220                     225 | 726 |
| gca tgg cca cat gag aag aac cag att ggt ttc aac tcc aat tct ctc<br>Ala Trp Pro His Glu Lys Asn Gln Ile Gly Phe Asn Ser Asn Ser Leu<br>230                   235                       240 | 774 |
| agc ata aga gga gga aat ttt gta ggc aat tat caa aac aaa aag gta<br>Ser Ile Arg Gly Gly Asn Phe Val Gly Asn Tyr Gln Asn Lys Lys Val<br>245                   250                       255                260 | 822 |
| gag ggg aag gca caa gga agc tct cat ggg cta cca aag aag gat gcg<br>Glu Gly Lys Ala Gln Gly Ser Ser His Gly Leu Pro Lys Lys Asp Ala<br>                         265                        270                    275 | 870 |
| ctg agt ggg tca gat tcg<br>Leu Ser Gly Ser Asp Ser<br>        280 | 888 |

<210> SEQ ID NO 2
<211> LENGTH: 282
<212> TYPE: PRT
<213> ORGANISM: Arabidopsis thaliana

<400> SEQUENCE: 2

Met Glu Glu Ile Ser Thr Asp Pro Val Val Pro Ala Val Lys Pro Asp
1               5                   10                 15

Pro Arg Thr Ser Ser Val Gly Glu Gly Ala Asn Arg His Glu Asn Asp
                  20                   25                  30

Asp Gly Gly Ser Gly Gly Ser Glu Ile Gly Ala Pro Asp Leu Asp Lys
              35                   40                   45

Asp Leu Leu Cys Pro Ile Cys Met Gln Ile Ile Lys Asp Ala Phe Leu
50                   55                   60

Thr Ala Cys Gly His Ser Phe Cys Tyr Met Cys Ile Ile Thr His Leu
65              70                   75                   80

Arg Asn Lys Ser Asp Cys Pro Cys Ser Gln His Leu Thr Asn Asn
                  85                   90                  95

Gln Leu Tyr Pro Asn Phe Leu Leu Asp Lys Leu Leu Lys Lys Thr Ser
                100                 105                110

Ala Arg His Val Ser Lys Thr Ala Ser Pro Leu Asp Gln Phe Arg Glu
            115                120                125

Ala Leu Gln Arg Gly Cys Asp Val Ser Ile Lys Glu Val Asp Asn Leu
      130                135                140

Leu Thr Leu Leu Ala Glu Arg Lys Arg Lys Met Glu Gln Glu Glu Ala
145              150                   155                 160

Glu Arg Asn Met Gln Ile Leu Leu Asp Phe Leu His Cys Leu Arg Lys
                165                 170                175

Gln Lys Val Asp Glu Leu Asn Glu Val Gln Thr Asp Leu Gln Tyr Ile
            180                185                190

Lys Glu Asp Ile Asn Ala Val Glu Arg His Arg Ile Asp Leu Tyr Arg

-continued

```
                195                 200                 205
Ala Arg Asp Arg Tyr Ser Val Lys Leu Arg Met Leu Gly Asp Asp Pro
    210                 215                 220

Ser Thr Arg Asn Ala Trp Pro His Glu Lys Asn Gln Ile Gly Phe Asn
225                 230                 235                 240

Ser Asn Ser Leu Ser Ile Arg Gly Gly Asn Phe Val Gly Asn Tyr Gln
                245                 250                 255

Asn Lys Lys Val Glu Gly Lys Ala Gln Gly Ser Ser His Gly Leu Pro
                260                 265                 270

Lys Lys Asp Ala Leu Ser Gly Ser Asp Ser
            275                 280
```